United States Patent
Apostolopoulos et al.

(10) Patent No.: US 12,059,195 B2
(45) Date of Patent: Aug. 13, 2024

(54) SEAL CONFIGURATIONS FOR SURGICAL INSTRUMENTS SUCH AS FOR USE IN ROBOTIC SURGICAL SYSTEMS

(71) Applicant: Covidien LP, Mansfield, MA (US)

(72) Inventors: Haralambos P. Apostolopoulos, Castle Rock, CO (US); Russell W. Holbrook, Longmont, CO (US); Jason G. Weihe, Longmont, CO (US); Zachary S. Heiliger, Nederland, CO (US); Dylan R. Kingsley, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 539 days.

(21) Appl. No.: 16/915,528

(22) Filed: Jun. 29, 2020

(65) Prior Publication Data

US 2021/0401487 A1 Dec. 30, 2021

(51) Int. Cl.
*A61B 18/14* (2006.01)
*A61B 17/00* (2006.01)
(Continued)

(52) U.S. Cl.
CPC ........... *A61B 18/1445* (2013.01); *A61B 2017/00398* (2013.01); *A61B 2017/2908* (2013.01);
(Continued)

(58) Field of Classification Search
CPC ............. A61B 18/1445; A61B 34/30; A61B 2017/00398; A61B 2017/2908;
(Continued)

(56) References Cited

U.S. PATENT DOCUMENTS

| 5,752,973 A | 5/1998 | Kieturakis |
| 5,792,135 A | 8/1998 | Madhani et al. |

(Continued)

FOREIGN PATENT DOCUMENTS

| EP | 2095778 A1 | 9/2009 |
| EP | 3300678 A1 | 4/2018 |

(Continued)

OTHER PUBLICATIONS

Extended European Search Report issued in corresponding European Application No. 21181512.1 dated Nov. 22, 2021, 9 pages.

*Primary Examiner* — Tan-Uyen T Ho
*Assistant Examiner* — David P Stein
(74) *Attorney, Agent, or Firm* — Carter, DeLuca & Farrell LLP

(57) ABSTRACT

A robotic surgical instrument includes a housing and a shaft extending distally from the housing and including proximal and distal segments and an articulating portion interconnecting the segments. An end effector assembly is coupled to the distal segment and a plurality of actuation components extends through at least a portion of the shaft to enable selective actuation of the end effector assembly. A seal configuration is operably associated with a proximal body portion of a proximal link of the articulating portion of the shaft to establish seals against an interior annular surface of the shaft, about each actuation component of the plurality of actuation components, and within a distal end portion of the proximal segment of the shaft to inhibit fluid communication proximally into the proximal segment of the shaft.

19 Claims, 21 Drawing Sheets

(51) Int. Cl.
  *A61B 17/29* (2006.01)
  *A61B 18/00* (2006.01)
  *A61B 34/30* (2016.01)
(52) U.S. Cl.
  CPC ............... *A61B 2017/2948* (2013.01); *A61B 2018/0063* (2013.01); *A61B 2018/1455* (2013.01); *A61B 34/30* (2016.02)
(58) Field of Classification Search
  CPC .... A61B 2017/2948; A61B 2018/0063; A61B 2018/1455; A61B 34/71; A61B 34/37; A61B 2017/00477
  See application file for complete search history.

(56) References Cited

U.S. PATENT DOCUMENTS

| | | | |
|---|---|---|---|
| 5,810,876 A * | 9/1998 | Kelleher | A61B 10/06 606/205 |
| 5,848,986 A | 12/1998 | Lundquist et al. | |
| 6,817,974 B2 | 11/2004 | Cooper et al. | |
| 7,799,028 B2 | 9/2010 | Schechter et al. | |
| 7,861,906 B2 | 1/2011 | Doll et al. | |
| 7,918,230 B2 | 4/2011 | Whitman et al. | |
| 8,579,176 B2 | 11/2013 | Smith et al. | |
| 9,055,961 B2 | 6/2015 | Manzo et al. | |
| 9,474,569 B2 | 10/2016 | Manzo et al. | |
| 10,973,600 B2 * | 4/2021 | Bruehwiler | A61B 34/71 |
| 2002/0099371 A1 | 7/2002 | Schulze et al. | |
| 2002/0177842 A1 | 11/2002 | Weiss | |
| 2003/0125734 A1 | 7/2003 | Mollenauer | |
| 2003/0208186 A1 | 11/2003 | Moreyra | |
| 2006/0022015 A1 | 2/2006 | Shelton et al. | |
| 2006/0025811 A1 | 2/2006 | Shelton | |
| 2007/0233052 A1 | 10/2007 | Brock | |
| 2007/0282358 A1 | 12/2007 | Remiszewski et al. | |
| 2008/0015631 A1 | 1/2008 | Lee et al. | |
| 2010/0016852 A1 | 1/2010 | Manzo et al. | |
| 2010/0168510 A1 | 7/2010 | Rogers et al. | |
| 2010/0274265 A1 | 10/2010 | Wingardner et al. | |
| 2010/0292691 A1 | 11/2010 | Brogna | |
| 2011/0118707 A1 | 5/2011 | Burbank | |
| 2011/0118708 A1 | 5/2011 | Burbank et al. | |
| 2011/0118709 A1 | 5/2011 | Burbank | |
| 2011/0118754 A1 | 5/2011 | Dachs, II et al. | |
| 2012/0209289 A1 * | 8/2012 | Duque | A61B 34/37 606/130 |
| 2016/0066982 A1 | 3/2016 | Marczyk et al. | |
| 2021/0315660 A1 * | 10/2021 | Williams | A61B 34/35 |

FOREIGN PATENT DOCUMENTS

| | | | |
|---|---|---|---|
| EP | 3616644 A1 | 3/2020 | |
| WO | WO-2011024888 A1 * | 3/2011 | ............. A61B 34/70 |
| WO | 2017136710 A2 | 8/2017 | |

* cited by examiner

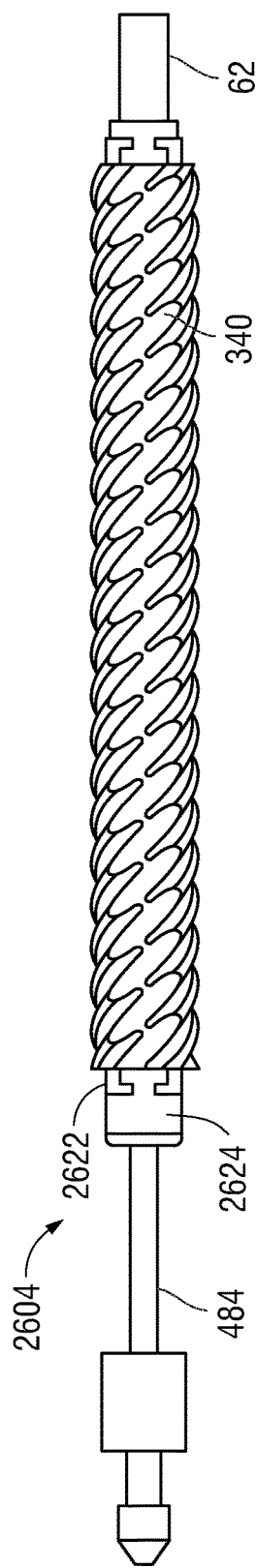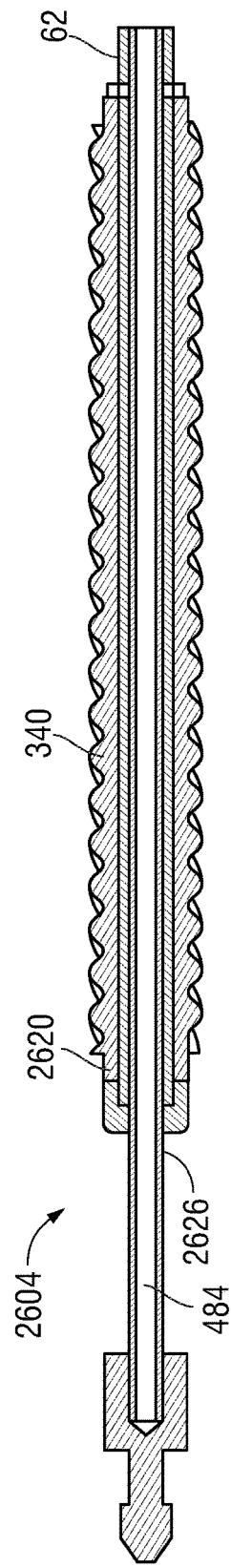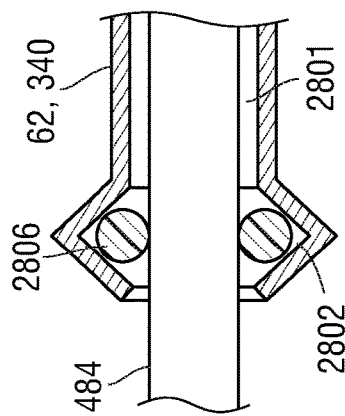

SEAL CONFIGURATIONS FOR SURGICAL INSTRUMENTS SUCH AS FOR USE IN ROBOTIC SURGICAL SYSTEMS

FIELD

The present disclosure relates to surgical instruments and, more specifically, to seal configurations for surgical instruments such as, for example, for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The surgical instruments or portions thereof may be configured as single-use instruments or portions that are discarded after use, or may be configured as reusable instruments or portions that are cleaned and sterilized between uses. Regardless of the configurations of the surgical instruments, the console and robotic arm are capital equipment configured for long-term, repeated use. The console and robotic arm may be protected by a sterile barrier during use and/or wiped clean after use to ensure cleanliness for subsequent uses.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%.

In order to inhibit fluid from traveling proximally from a surgical instrument and/or to inhibit fluid from traveling from a more-distal portion of a surgical instrument to a more-proximal portion thereof, the present disclosure provides various seal configurations and surgical instruments including one or more seal configurations incorporated into the surgical instruments. Thus, the aspects and features of the present disclosure help to prevent contamination of capital equipment and other surgical instruments or portions thereof disposed proximally of the seal configurations. To the extent consistent, any of the aspects described herein may be used in conjunction with any or all of the other aspects described herein.

Provided in accordance with aspects of the present disclosure is a robotic surgical instrument including a housing, a support plate disposed within the housing, a shaft, an end effector assembly, a plurality of actuation components, and a seal configuration. The shaft has a proximal end portion coupled to the support plate within the housing. The shaft extends distally from the housing and includes a proximal segment, a distal segment, and an articulating portion interconnecting the proximal and distal segments. The end effector assembly is coupled to the distal segment of the shaft and extends distally therefrom. The plurality of actuation components extends through the support plate and at least a portion of the shaft to operably couple to at least one of: the end effector assembly, the articulating portion, or the distal segment to enable selective actuation of the end effector assembly. The seal configuration establishes seals against an interior annular surface of the shaft, about each actuation component of the plurality of actuation components, and within the proximal end portion of the shaft to inhibit fluid communication from the shaft into the housing.

In an aspect of the present disclosure, the support plate at least partially supports an actuation assembly configured to drive at least one actuation component of the plurality of actuation components. In such aspects, the actuation assembly may include a plurality of gears operably coupled between at least one rotational input and the at least one actuation component of the plurality of actuation components.

In another aspect of the present disclosure, the plurality of actuation components includes at least two or each of: a plurality of articulation cables; one or more electrical lead wires; or a drive tube.

In yet another aspect of the present disclosure, the seal configuration includes a seal having a distal body extending through the support plate and into the proximal end portion of the shaft, and a proximal portion proximally abutting the support plate. The seal configuration further includes a lock plate configured to engage the support plate with the proximal flange of the seal therebetween to thereby lock the seal in position. The lock plate defines at least one opening to permit passage of the plurality of actuation components therethrough.

In still another aspect of the present disclosure, the proximal flange of the seal defines an inner aperture and a plurality of radial apertures each configured to receive one actuation component of the plurality of actuation components. In such aspects, the distal body of the seal may define an inner aperture communicating with the inner aperture of the proximal flange, and/or a plurality of radial channels communicating with the plurality of radial apertures of the proximal flange.

In still yet another aspect of the present disclosure, the proximal end portion of the shaft is secured directly to the support plate. In such aspects, the seal configuration may include an enlarged portion of the proximal end portion of the shaft that defines a diameter larger than a diameter of a body portion of the proximal segment of the shaft. The seal configuration may further include a seal disposed within the enlarged portion, which may be a multi-part seal.

In another aspect of the present disclosure, the seal configuration includes a connector shaft that secures the proximal end portion of the shaft to the support plate and defines a diameter larger than a diameter of the proximal end portion of the shaft. In such aspects, the seal configuration may further include a seal disposed within the connector shaft, which may be a multi-part seal.

In yet another aspect of the present disclosure, the seal configuration includes a seal disposed within the proximal end portion of the shaft and at least one retention feature defined on the proximal end portion of the shaft to inhibit movement of the seal. The at least one retention feature may include, for example, a lock ring, ribs, or protrusions.

In still another aspect of the present disclosure, the seal includes at least one complementary retention feature. For example, the at least one retention feature may be at least one aperture and the at least one complementary retention feature is at least one protrusion engaged within the at least one aperture.

In still yet another aspect of the present disclosure, the seal configuration includes an injected seal material injected into at least one of the proximal end portion of the shaft or the housing.

In another aspect of the present disclosure, actuating the end effector assembly includes at least one of: articulating the end effector assembly; manipulating the end effector assembly; advancing a component through the end effector assembly; or energizing the end effector assembly.

Another robotic surgical instrument provided in accordance with aspects of the present disclosure includes a housing, a shaft extending distally from the housing and including a proximal segment, a distal segment, and an articulating portion interconnecting the proximal and distal segments, an end effector assembly, a plurality of actuation components, and a seal configuration. The articulating portion includes a proximal link having a proximal body portion configured for at least partial receipt within the proximal segment of the shaft and a distal pivoting portion configured to pivotably couple to a more-distal link of the articulating portion. The end effector assembly is coupled to the distal segment of the shaft and extends distally therefrom. The plurality of actuation components extends through at least a portion of the shaft to operably couple to at least one of: the end effector assembly, the articulating portion, or the distal segment to enable selective actuation of the end effector assembly. The seal configuration is operably associated with the proximal body portion of the proximal link of the articulating portion of the shaft to establish seals against an interior annular surface of the shaft, about each actuation component of the plurality of actuation components, and within a distal end portion of the proximal segment of the shaft to inhibit fluid communication proximally into the proximal segment of the shaft.

In an aspect of the present disclosure, the plurality of actuation components includes at least two of, at least three of, or each of: a plurality of articulation cables; one or more electrical lead wires; a drive member; or a drive tube.

In another aspect of the present disclosure, actuating the end effector assembly includes at least one of: articulating the end effector assembly; manipulating the end effector assembly; advancing a component through the end effector assembly; or energizing the end effector assembly.

In yet another aspect of the present disclosure, the seal configuration includes a plug, a seal ring, and a clip. The plug is configured to engage the proximal body portion of the proximal link and the clip is configured to engage the plug with the seal ring disposed therebetween. In such aspects, the seal ring may be configured to establish the seals. More specifically, the seal ring may include a plurality of apertures each configured to sealingly receive one of the actuation components of the plurality of actuation components and/or an outer annular surface configured to seal against the inner annular surface of the shaft and/or an inner annular surface of the proximal link.

In still another aspect of the present disclosure, the seal configuration includes an engagement plug, and inner seal plug, and an outer seal ring. The engagement plug is configured to engage the proximal body portion of the proximal link with the inner seal plug and the outer seal ring disposed therebetween. In such aspects, the inner seal plug and the outer seal ring may be configured to cooperate to establish the seals. More specifically, the outer seal ring may include a plurality of apertures each configured to sealingly receive one of the actuation components of the plurality of actuation components and/or an outer annular surface configured to seal against the inner annular surface of the shaft.

Additionally or alternatively, the inner seal plug may include a plurality of apertures each configured to sealingly receive one of the actuation components of the plurality of actuation components.

In still yet another aspect of the present disclosure, the seal configuration includes a plug, an outer seal ring, and an o-ring seal. The plug is configured for engagement partially within the proximal body portion of the proximal link. The outer seal ring is configured for engagement about the plug and the proximal body portion of the proximal link. The o-ring seal is configured for positioning within the plug. In such aspects, the outer seal ring and the o-ring seal may be configured to establish the seals. More specifically, the outer seal ring may include a plurality of apertures each configured to sealingly receive one of the actuation components of the plurality of actuation components and/or the o-ring seal may be configured to sealingly engage one of the actuation components of the plurality of actuation components within a central lumen of the plug.

BRIEF DESCRIPTION OF THE DRAWINGS

Various aspects and features of the present disclosure are described hereinbelow with reference to the drawings wherein:

FIGS. 26A and 26B are side and longitudinal cross-sectional views, respectively, of a proximal portion of knife drive and jaw drive assemblies configured for use with the surgical instrument of FIG. 1 including seals in accordance with the present disclosure;

FIGS. 27 and 28 are longitudinal cross-sectional views of proximal portions of knife drive and jaw drive assemblies configured for use with the surgical instrument of FIG. 1 including seals in accordance with the present disclosure;

DETAILED DESCRIPTION

Figure 1:
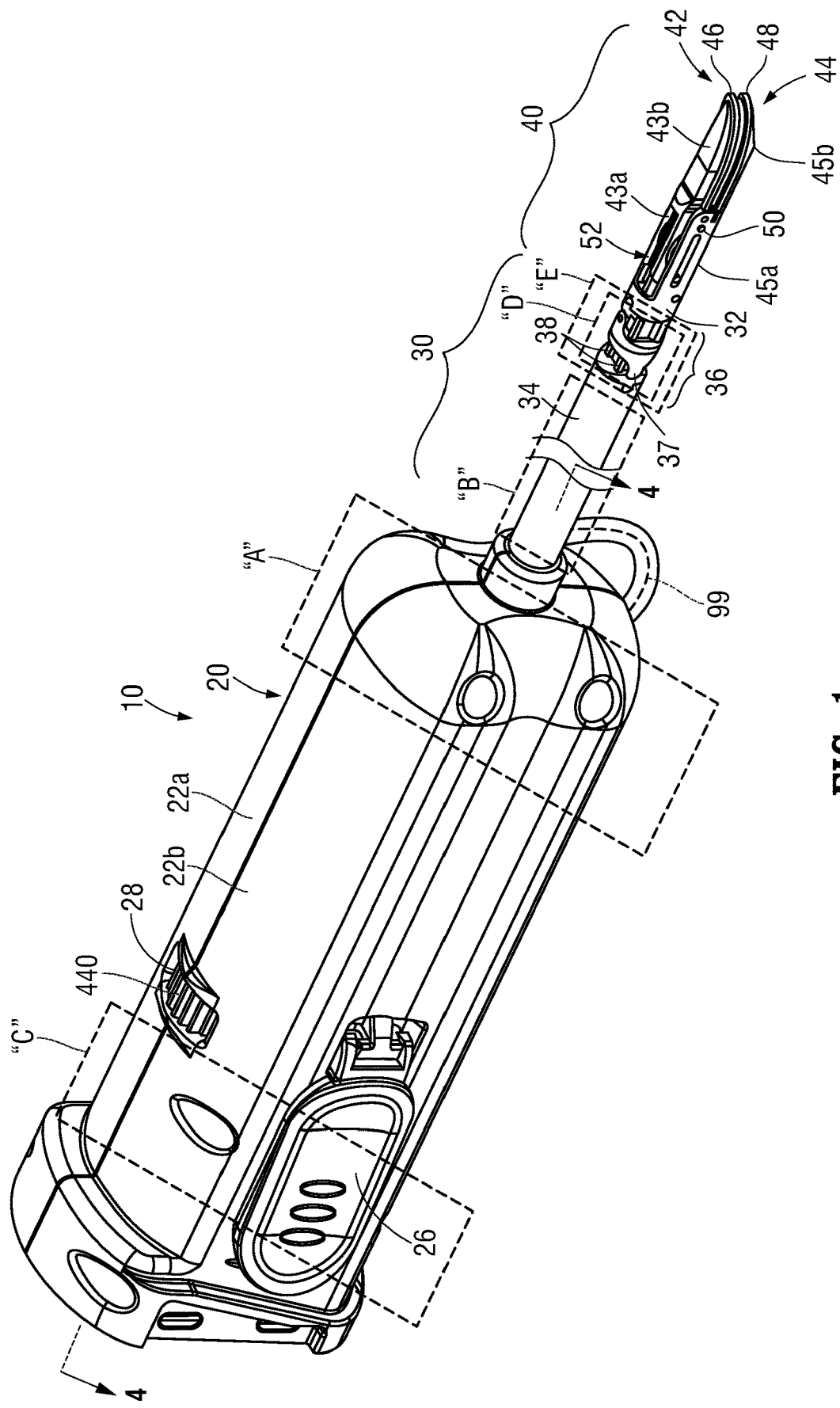
FIG. 1 is a perspective view of a surgical instrument provided in accordance with the present disclosure configured for mounting on a robotic arm of a robotic surgical system.
Figure 2A:
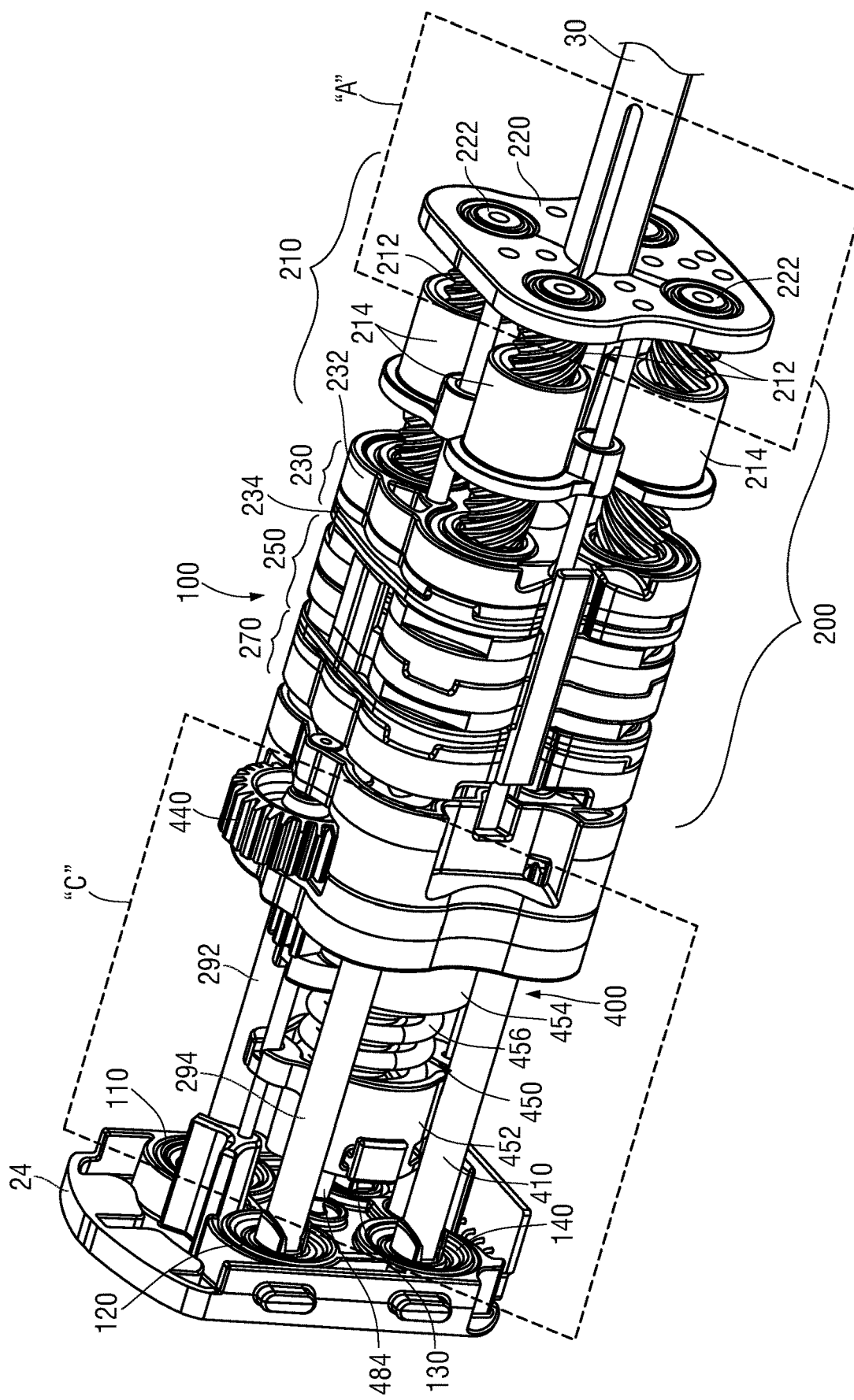
FIG. 2A is a front perspective view of a proximal portion of the surgical instrument of FIG. 1 with an outer housing removed.
Figure 2B:
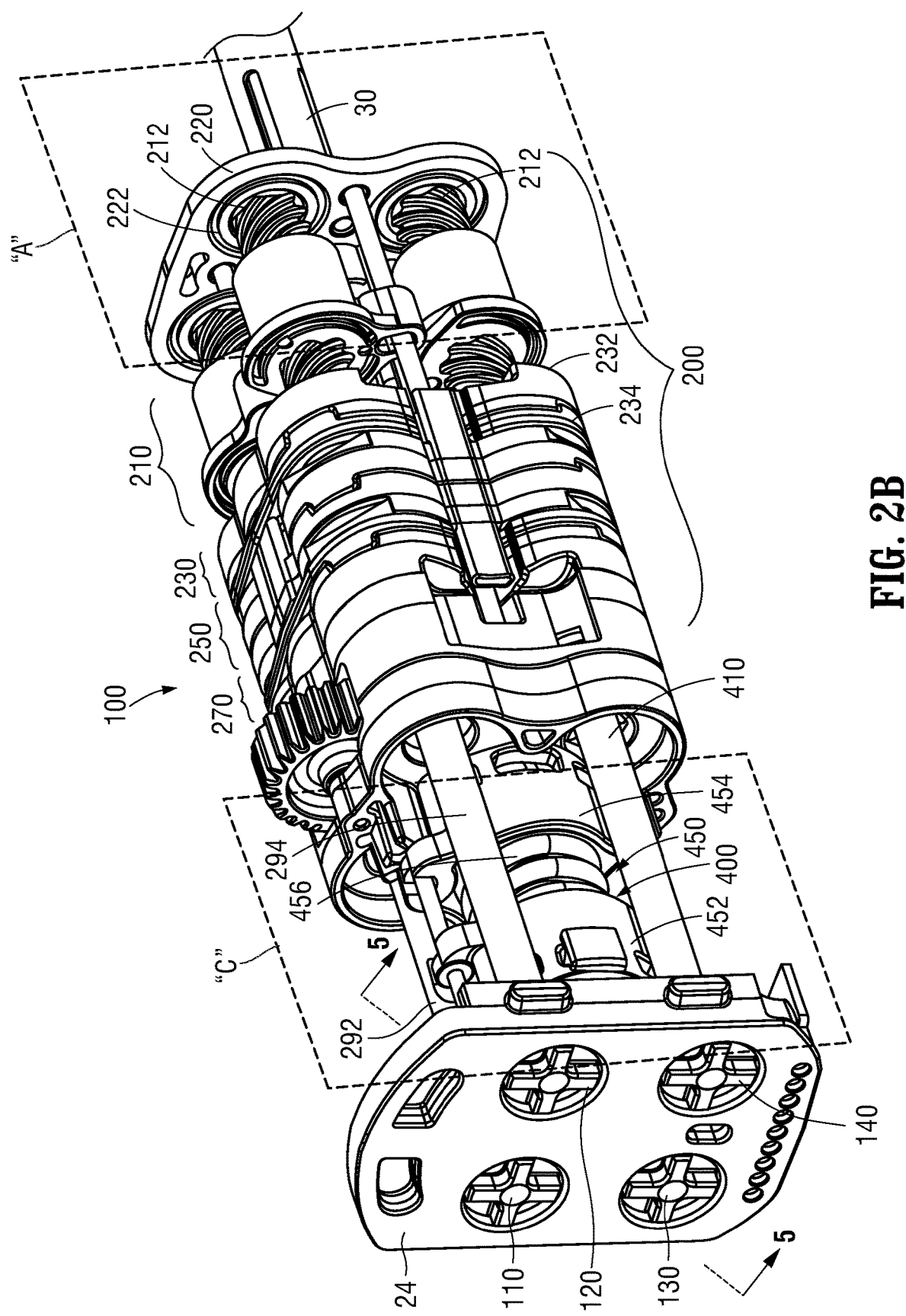
FIG. 2B is a rear perspective view of the proximal portion of the surgical instrument of FIG. 1 with the outer housing removed.
Figure 2C:
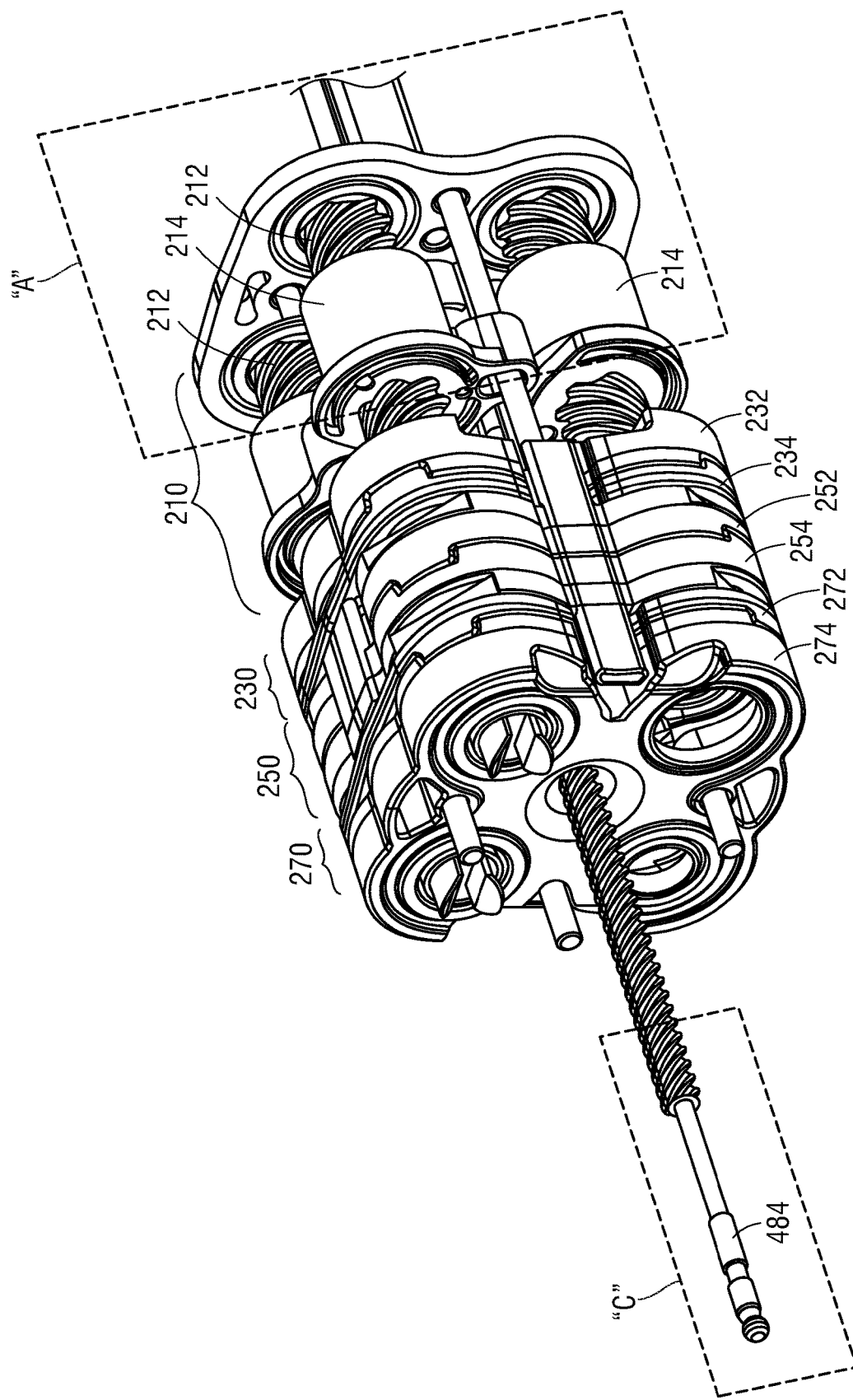
FIG. 2C is a rear perspective view of the proximal portion of the surgical instrument of FIG. 1 with the outer housing and proximal components of the actuation assembly removed.
Figure 3:
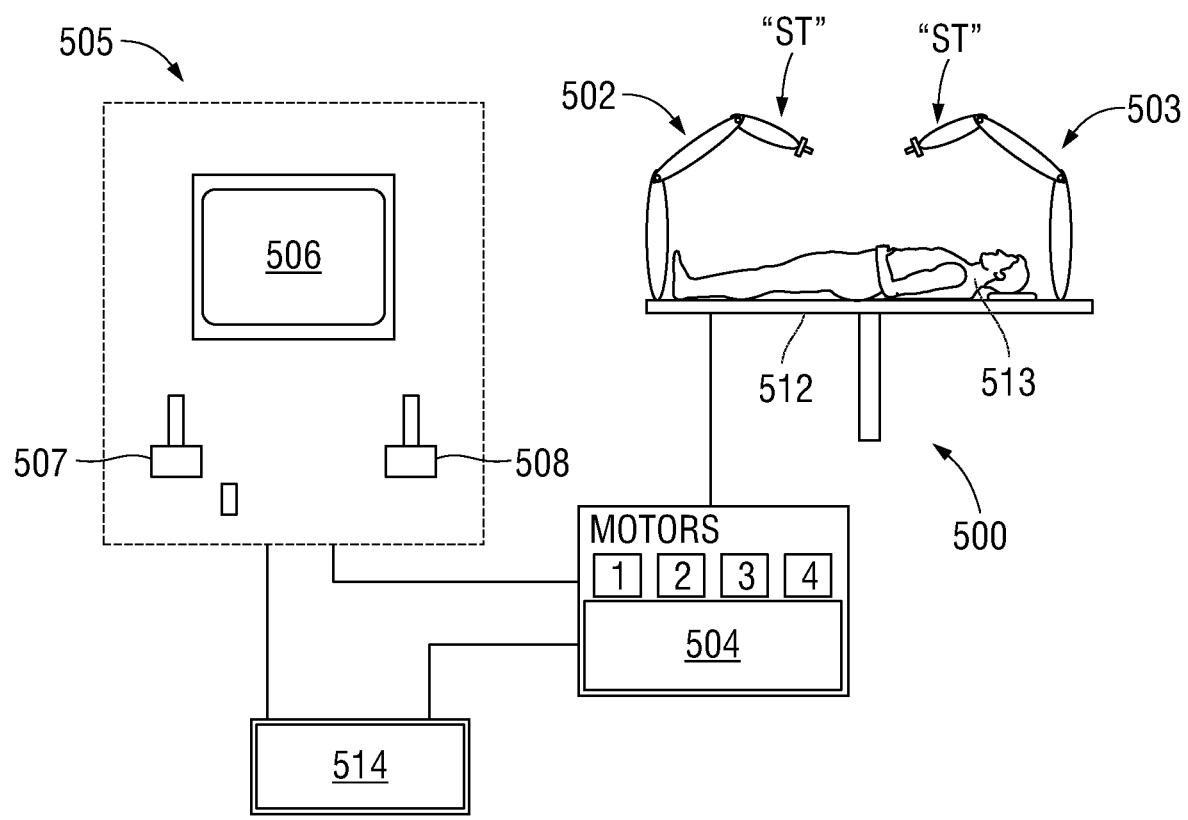
FIG. 3 is a schematic illustration of an exemplary robotic surgical system configured to releasably receive the surgical instrument of FIG. 1.

Referring to FIGS. 1-2C, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments and/or in other suitable surgical systems.

Housing 20 of instrument 10 includes first and second body portion 22a, 22b and a proximal face plate 24 that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extends outwardly from opposing sides of housing 20 and enables releasable engagement of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

End effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Figure 4:
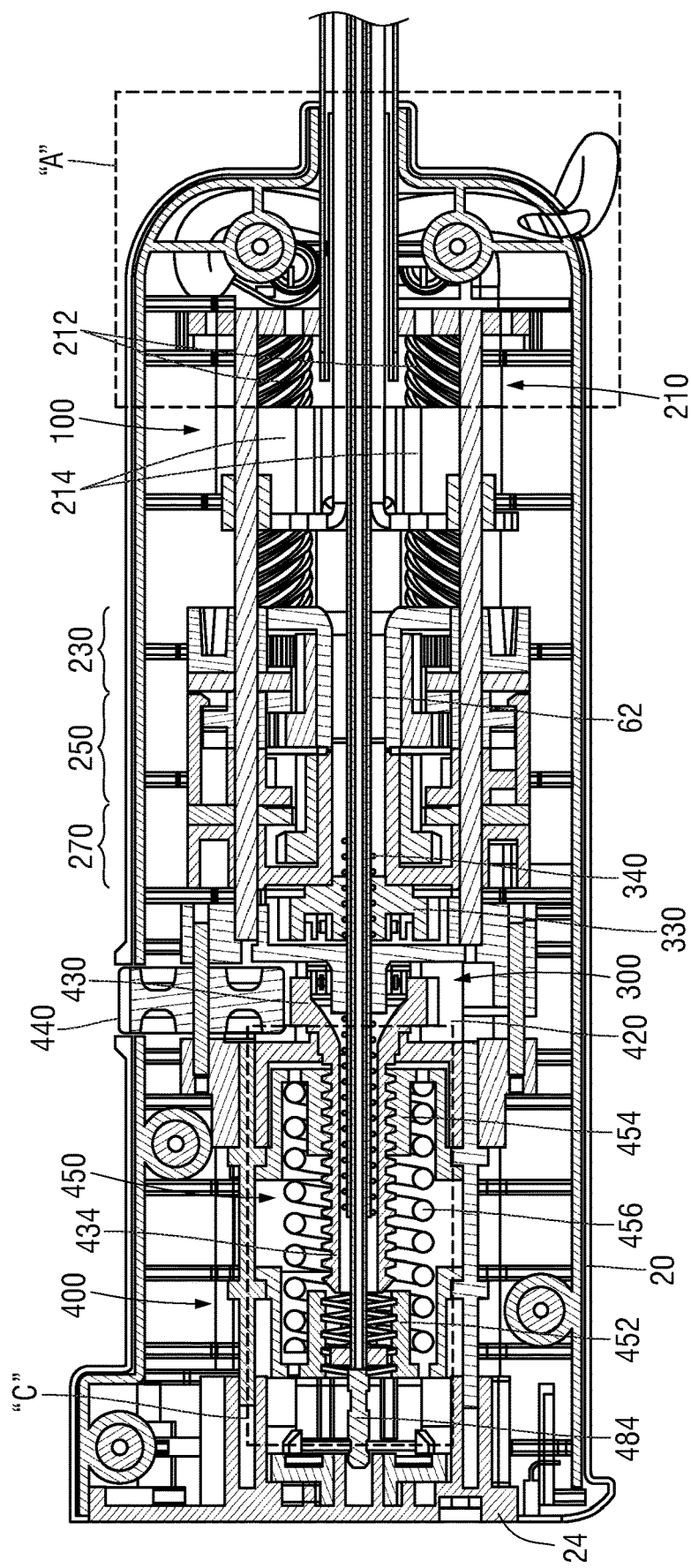
FIG. 4 is a longitudinal cross-sectional view taken along section line "4-4" of FIG. 1.

In some configurations, longitudinally-extending knife channels (not shown) are defined through tissue-contacting surfaces 46, 48, respectively, of jaw members 42, 44. In such configurations, a knife assembly 60 is provided that includes a proximal knife drive tube 62, a distal knife rod 64, an intermediate elongated collar 66, and a knife blade 68 (see FIGS. 26A, 26B and 29A). The connector components 62-66 of knife assembly 60 (see FIGS. 26A, 26B and 29A) extend from housing 20 through shaft 30 to end effector assembly 40. Knife blade 68 (FIG. 29A) is disposed within end effector assembly 40 between jaw members 42, 44 is provided to enable cutting of tissue grasped between tissue-contacting surfaces 46, 48 of jaw members 42, 44, respectively. Proximal knife tube 62 (FIGS. 4 and 26A-26B) is operably coupled to a knife drive assembly 300 of actuation assembly 100 (FIGS. 2A and 2B) at a proximal end thereof to enable selective actuation thereof to, in turn, reciprocate the knife blade 68 (FIG. 29A) between jaw members 42, 44 to cut tissue grasped between tissue-contacting surfaces 46, 48.

Continuing with reference to FIGS. 1-2C, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive assembly 400 of actuation assembly 100 (FIGS. 2A and 2B) to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines a conductive pathway (not shown) through housing 20 and shaft 30 to end effector assembly 40 that may include lead wires 99, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48.

Figure 5:
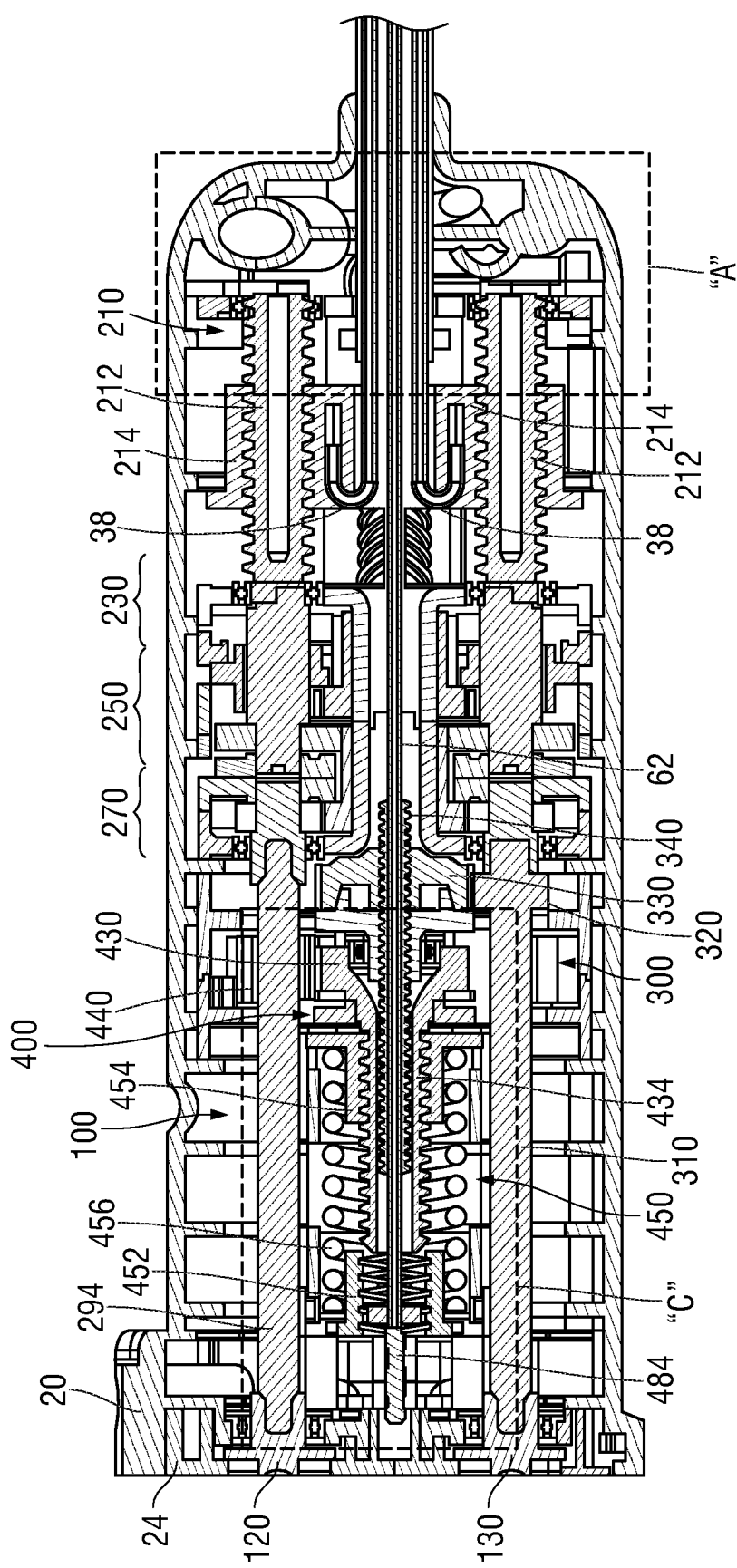
FIG. 5 is a longitudinal cross-sectional view taken along section line "5-5" of FIG. 2B.

As noted above, actuation assembly 100 is disposed within housing 20 and includes an articulation assembly 200, a knife drive assembly 300, and a jaw drive assembly 400. Articulation assembly 200 is operably coupled between first and second inputs 110, 120, respectively, of actuation assembly 100 and articulation cables 38 (FIG. 1) such that, upon receipt of appropriate rotational inputs into first and/or second inputs 110, 120, articulation assembly 200 manipulates cables 38 (FIGS. 1 and 5) to articulate end effector assembly 40 in a desired direction, e.g., to pitch and/or yaw end effector assembly 40. Knife drive assembly 300 is operably coupled between third input 130 of actuation assembly 100 and knife tube 62 (FIGS. 26A and 26B) such that, upon receipt of appropriate rotational input into third input 130, knife drive assembly 300 manipulates knife tube 62 to reciprocate the knife blade 68 (FIG. 29A) between jaw members 42, 44 to cut tissue grasped between tissue-contacting surfaces 46, 48. Jaw drive assembly 400 is operably coupled between fourth input 140 of actuation assembly 100 and drive rod 484 such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 5 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

With reference to FIGS. 1, 2A-2C, 4, and 5, articulation assembly 200 of actuation assembly 100 including a lead screw sub-assembly 210, a first gear sub-assembly 230, a second gear sub-assembly 250, a third gear sub-assembly 270, and first and second input shafts 292, 294. Although articulation assembly 200 is detailed herein as including a plurality of gears, such gearing components may be replaced or supplemented with the use of belts instead of directly meshed gears, without departing from the present disclosure. Further, multiple gears (and/or belts) may be provided in place of single gears (and/or belts) to provide a desired amplification or attenuation effect.

Lead screw sub-assembly 210 of actuation assembly 100 includes four lead screws 212 arranged to define a generally square configuration wherein diagonally-opposed lead screws 212 define opposite thread-pitch directions. Each lead screw 212 includes a collar 214 threadingly engaged thereabout such that rotation of the lead screw 212 translates the corresponding collar 214 longitudinally therealong. Each collar 214, in turn, secures a proximal end portion of one of the articulation cables 38 therein, e.g., via a crimp or other suitable engagement (mechanical fastening, adhesion, welding, etc.). Thus, distal translation of a collar 214 slackens the corresponding articulation cable 38 by pushing the corresponding articulation cable 38 in a distal direction, while proximal translation of a collar 214 tensions the corresponding articulation cable 38 by pulling the corresponding articulation cable 38 in a proximal direction.

Lead screw sub-assembly 210 further includes a distal plate 220 including four bushings 222 each of which rotatably retains the distal end portion of one of the four lead screws 212. The proximal end portions of lead screws 212 define keyed, e.g., semi-circular inputs, such that rotational inputs provided thereto similarly rotate the lead screws 212. In some configurations, a proximal end portion of shaft 30 is fixedly engaged (directly or indirectly) with distal plate 220.

First gear sub-assembly 230 includes a distal housing body 232 and a proximal housing body 234 that cooperate to operably support a first pair of diagonally-opposed gears mounted on keyed outputs such that such that rotation of one of the gears rotates the corresponding keyed output. The proximal end portions of a first diagonally-opposed pair of lead screws 212 of lead screw sub-assembly 210 are engaged with corresponding keyed outputs of first gear sub-assembly 230, thereby rotatably coupling each of the gears of first gear sub-assembly 230 with one of the lead screws 212 of the first diagonally-opposed pair of lead screws 212 such that rotation of one of the gears rotates the corresponding lead screw 212.

Second gear sub-assembly 250 includes a distal housing body 252 and a proximal housing body 254 that cooperate to operably support a second pair of diagonally-opposed gears mounted on keyed outputs, a central compound gear, and a first coupling gear mounted on a first coupling shaft. The first coupling gear 264 is disposed in meshed engagement with a proximal gear of the central compound gear.

The first diagonal pair of articulation cables 38 is pre-tensioned prior to engagement of second gear sub-assembly 250 with first gear sub-assembly 230. Upon such engagement, the keyed outputs of second gear sub-assembly 250 are rotationally coupled with the proximal end portions of the second diagonally-opposed pair of lead screws 212, thereby rotatably coupling each of the gears of second gear sub-assembly 250 with one of the lead screws 212 of the second diagonally-opposed pair of lead screws 212 such that rotation of one of the gears rotates the corresponding lead screw 212. Engagement of second gear sub-assembly 250 with first gear sub-assembly 230 also disposes a distal gear of the central compound gear into meshed engagement with and between the diagonally-opposed gears of first gear sub-assembly 230 to thereby couple the diagonally-opposed gears with one another, coupling the lead screws 212 of the first diagonally-opposed pair of lead screws 212 with one another and locking in the pre-tension of the first pair of articulation cables 38.

Third gear sub-assembly 270 includes a distal housing body 272 and a proximal housing body 274 that operably support a central compound gear and a second coupling gear mounted on a second coupling shaft. The second coupling shaft includes the second coupling gear mounted thereon and has a proximal end portion that defines a keyed input. Prior to engagement of third gear sub-assembly 270 with second gear sub-assembly 250, the second diagonal pair of articulation cables 38 is pre-tensioned. Once the pre-tension threshold for the second diagonal pair of articulation cables 38 is reached, third gear sub-assembly 270 is engaged with second gear sub-assembly 250 such that a distal gear of the central compound gear of third gear sub-assembly 270 is disposed in meshed engagement with and between the second pair of diagonally-opposed gears of second gear sub-assembly 250 to couple the diagonally-opposed gears with one another, thereby coupling the second diagonally-opposed pair of lead screws 212 with one another, and locking the pre-tension on the second pair of articulation cables 38.

With first, second, and third gear sub-assemblies 230, 250, 270, respectively, assembled with one another and lead screw sub-assembly 210, as detailed above, input shafts 292, 294 can be connected between inputs 110, 120 and the keyed outputs of first and second gear sub-assemblies 230, 240, respectively. Thus, in use, rotational input provided to inputs 110, 120 can be utilized to move collars 214 about lead screws 212 in diagonal pairs. Depending upon the direction of rotational input provided to inputs 110, 120 and whether the inputs to the pairs are the same or opposite, pitch articulation (in either direction), yaw articulation (in either direction), and/or any combination thereof can be achieved. Articulation assembly 200 is described in greater detail in U.S. patent application Ser. No. 16/395,748, titled "ARTICULATION ASSEMBLY FOR A SURGICAL INSTRUMENT SUCH AS FOR USE IN A ROBOTIC SURGICAL SYSTEM AND METHODS OF ASSEMBLING THE SAME," filed on Apr. 26, 2019.

Continuing with reference to FIGS. 1, 2A-2C, 4, and 5, knife drive assembly 300 includes an input shaft 310, an input gear 320 engaged on input shaft 310, a central gear 330 defining external threading disposed in meshed engagement with input gear 320 and internal threading, and a lead screw 340 extending through the central gear 330 in meshed engagement with the internal threading thereof. As a result of this configuration, a rotational input provided to third input 130 rotates input shaft 310, thereby rotating input gear 320 to, in turn, rotate central gear 330, which results in translation of lead screw 340. Lead screw 340 is fixedly engaged about a proximal end portion of knife tube 62 such that translation of lead screw 340 translates knife tube 62, e.g., to thereby translate the knife blade 68 (FIG. 29A) between jaw members 42, 44 (FIG. 1) to cut tissue grasped therebetween. Lead screw 340 and knife tube 62 are coaxially disposed about drive rod 484.

Jaw drive assembly 400 includes an input shaft 410 operably coupled to fourth input 140 at a proximal end portion thereof, an input gear 420 fixedly engaged on input shaft 410 at a distal end portion thereof, a drive gear 430 disposed in meshed engagement with input gear 420, a thumbwheel 440 disposed in meshed engagement with drive gear 430, a lead screw 434 is fixedly engaged, e.g., monolithically formed with, drive gear 430, and a spring force assembly 450 operably coupling lead screw 434 with drive rod 484. Spring force assembly 450 includes a proximal hub 452 engaged with a proximal end portion of drive rod 484, a distal hub 454 threadingly engaged about lead screw 434, and a compression spring 456 disposed between proximal and distal hubs 452, 454, respectively. As a result of this configuration, in response to an input to close end effector assembly 40, e.g., rotational input to fourth input 140 or a manual input to rotation wheel 440, drive shaft 410 is rotated to thereby rotate input gear 420 which, in turn, rotates drive gear 430 such that distal hub 454 is translated proximally towards proximal hub 452. Initially, where forces resisting approximation of jaw members 42, 44 are below a threshold corresponding to the spring value of compression spring 456, the closure force applied by jaw members 42, 44 is relatively 18w such that the urging of distal hub 454 proximally against compression spring 456 urges compression spring 456 proximally which, in turn, urges drive rod 484 proximally to pivot jaw member 42 relative to jaw member 44 from the spaced-apart position towards the approximated position to grasp tissue therebetween. Upon further approximation of jaw members 42, 44 to grasp tissue therebetween, the forces resisting approximation of jaw members 42, 44, e.g., tissue resisting compression, may reach the threshold and, thus the closure force applied by jaw members 42, 44 may reach a corresponding threshold. In order to maintain the closure force applied by jaw members 42, 44 within a closure force range such as, for example, from about 3 kg/cm$^2$ to about 16 kg/cm$^2$, application of further closure force by jaw members 42, 44 is inhibited beyond this point despite further rotational input to fourth input 140. More specifically, once the threshold has been reached, further rotational input to fourth input 140 rotates drive shaft 410, input gear 420, and drive gear 430 to translate distal hub 454 further proximally into compression spring 456. However, rather than compression spring 456 urging proximal hub 452 further proximally to continue approximation of jaw members 42, 44 and increase the closure force applied therebetween, compression spring 456 is compressed, enabling proximal hub 452 and, thus, drive rod 484 to remain in position despite the continued movement of distal hub 454, thus inhibiting application of additional closure force between jaw members 42, 44. With tissue grasped between jaw members 42, 44 under an appropriate closure force, energy may be supplied to jaw members 42, 44 to treat, e.g., seal tissue. Thereafter, the knife 68 (FIG. 29A) may be advanced between jaw members 42, 44 to cut the treated tissue.

Figure 6:
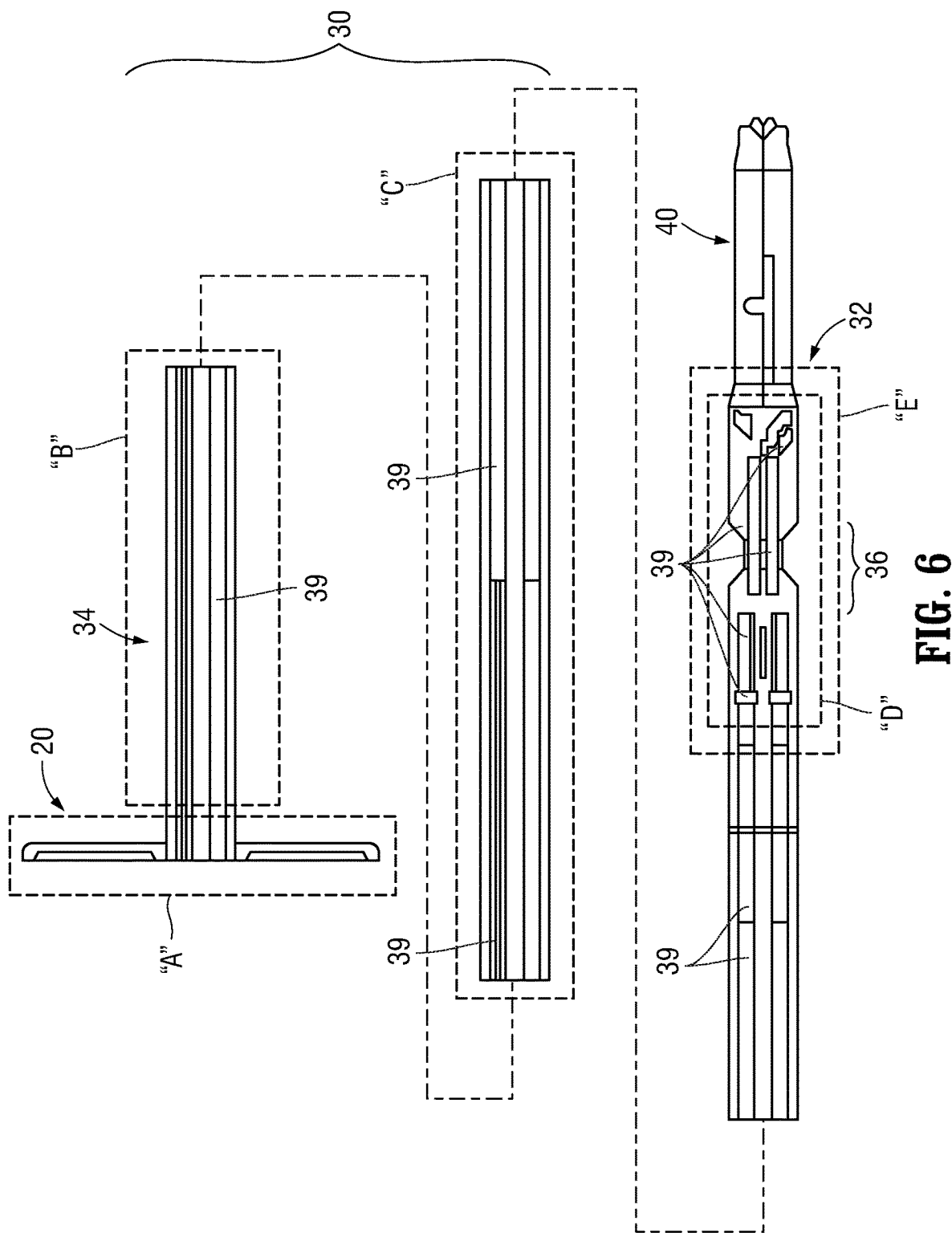
FIG. 6 is longitudinal cross-sectional view of a distal portion of the surgical instrument of FIG. 1.

Turning to FIG. 6, in conjunction with FIG. 1, as noted above, shaft 30 extends distally from housing 20 and includes distal segment 32, proximal segment 34, and articulating section 36. In some configurations, as also noted above, a proximal end portion of proximal segment 34 of shaft 30 extends into housing 20 wherein it is fixedly engaged (directly or indirectly) with distal plate 220 of articulation assembly 200 (see FIG. 2A) within housing 20. Articulation cables 38 (FIGS. 1, 4, and 5), knife tube 62 (FIGS. 4 and 5), and electrically-conductive structures (e.g., lead wires 99 (FIG. 1)) extend through proximal segment 34 of shaft 30 to articulating section 36, distal segment 32, or end effector assembly 40 to enable articulation of end effector assembly 40 in pitch and jaw directions and to enable operation of end effector assembly 40 to grasp, treat, and/or cut tissue. In order to provide support for these components extending through shaft 30 and maintain proper position, spacing, and/or orientation of these components extending through shaft 30, one or more internal structures 39 are disposed or formed within shaft 30. The one or more internal structures 39 may include, for example, any combination of one or more of supports, spacers, guides, bushings, etc., and may extend along a portion or the entirety of shaft 30 continuously or intermittently.

Referring generally to FIGS. 1-6, during use of instrument 10, fluids (blood, other bodily fluids, surgical fluids, etc., including fluids carrying tissue, surgical debris, etc.) from the surgical site may enter instrument 10, e.g., via end effector assembly 40, articulating section 36 of shaft 30, and/or at other locations, and travel proximally within and/or about shaft 30 towards or into housing 20. In order to protect capital equipment such as the robotic arm of the robotic surgical system, e.g., robotic surgical system 500 (FIG. 3), to which instrument 10 is mounted (and/or for other purposes such as, for example, to facilitate cleaning all or a portion of instrument 10 in preparation for reuse), the present disclosure provides various seal configurations (one-part seals, multi-part seals, plural seals, seal assemblies including one or more seals and one or more support/retention parts, etc.) disposed in various different locations along instrument 10 to inhibit proximally-traveling fluid from contaminating the robotic arm (and/or portions of instrument 10).

More specifically, one or more seals may be disposed at one or more of the following locations: location "A" at a proximal end portion of shaft 30 within or adjacent to housing 20; location "B" at one or more positions along a portion of proximal segment 34 of shaft 30; location "C" at or near proximal end portions of knife assembly 60, knife drive assembly 300, and/or jaw drive assembly 400; location "D" at or near distal end portions of knife assembly 60 and/or jaw drive assembly 400; and/or location "E" at or near articulating section 36 of shaft 30. Further, although a seal may be detailed herein for use at one location, it is contemplated that any such seals, to the extent practicable, may be used at any of the other identified locations or other suitable locations. Likewise, any suitable combination of seals at one or more of the identified locations and/or other suitable locations may be provided.

Figure 7:
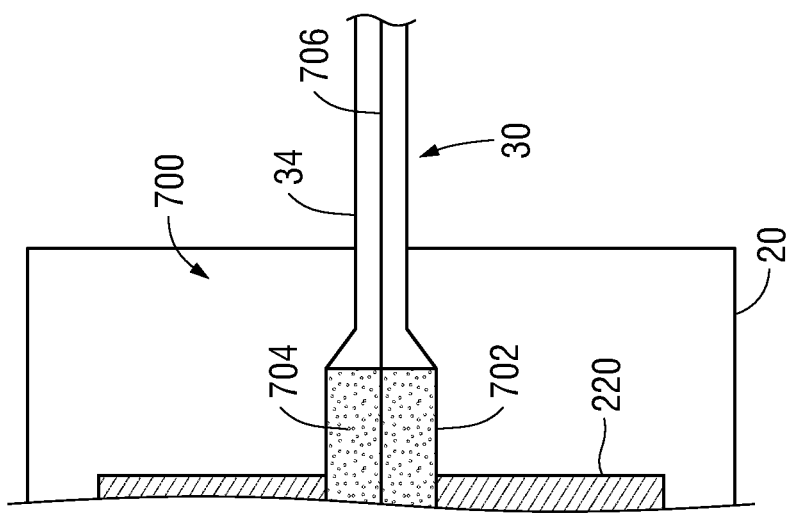
FIG. 7 is a longitudinal cross-sectional view of a proximal portion of a shaft configured for use with the surgical instrument of FIG. 1 including a seal in accordance with the present disclosure.

With reference to FIG. 7, a seal configuration 700 provided in accordance with the present disclosure is shown in use at location "A" (FIGS. 1, 2A-2C, and 6). More specifically, seal configuration 700 includes an enlarged proximal end portion 702 of proximal segment 34 of shaft 30 and a seal 704 disposed therein. Enlarged proximal end portion 702 is disposed within housing 20 and secured, e.g., welded or otherwise attached, to distal plate 220 of lead screw sub-assembly 210 (see FIGS. 2A-2C). Enlarged proximal end portion 702 defines a larger internal diameter as compared to the body of proximal segment 34 of shaft 30. The relatively larger internal diameter of enlarged proximal end portion 702 facilitates the manufacture of seal 704 and/or assembly of seal 704 within enlarged proximal end portion 702. Further, upon assembly, seal 704 is substantially retained in position within enlarged proximal end portion 702 of proximal segment 34 of shaft 30 as distal plate 220 inhibits substantial proximal movement of seal 704 while the smaller diameter body of proximal segment 34 of shaft 30 inhibits substantial distal movement of seal 704. Seal 704 may be formed as a solid piece of material, e.g., an elastomeric material, as a single piece of material that is inserted into enlarged proximal end portion 702 or multiple pieces of material coupled to one another before or during insertion into enlarged proximal end portion 702. In some configurations, seal 704 may include a greased or otherwise lubricated plug to facilitate insertion and formation of a seal. Grease or other lubrication may likewise be utilized to facilitate sealing with any of the other configurations detailed herein. Seal 704 may alternatively be a semi-solid material, e.g., a gel, or may be a material that is injected into enlarged proximal end portion 702 in one form, state, or condition before transitioning to another form, state, or condition e.g., foam, injectable silicone, etc. Combinations of the above may also be utilized. Regardless of the particular configuration of seal 704, seal 704 serves to establish a seal within enlarged proximal end portion 702 and about the actuation components 706 extending therethrough, e.g., articulation cables 38 (FIGS. 1, 4, and 5), knife tube 62 (FIGS. 4 and 5), and lead wires 99 (FIG. 1). Thus, seal 704 functions to inhibit the passage of fluids proximally across seal 704 while still enabling operation of the actuation components 706 extending therethrough. Other suitable configurations of seal 704 such as those detailed hereinbelow are also contemplated.

Figure 8:
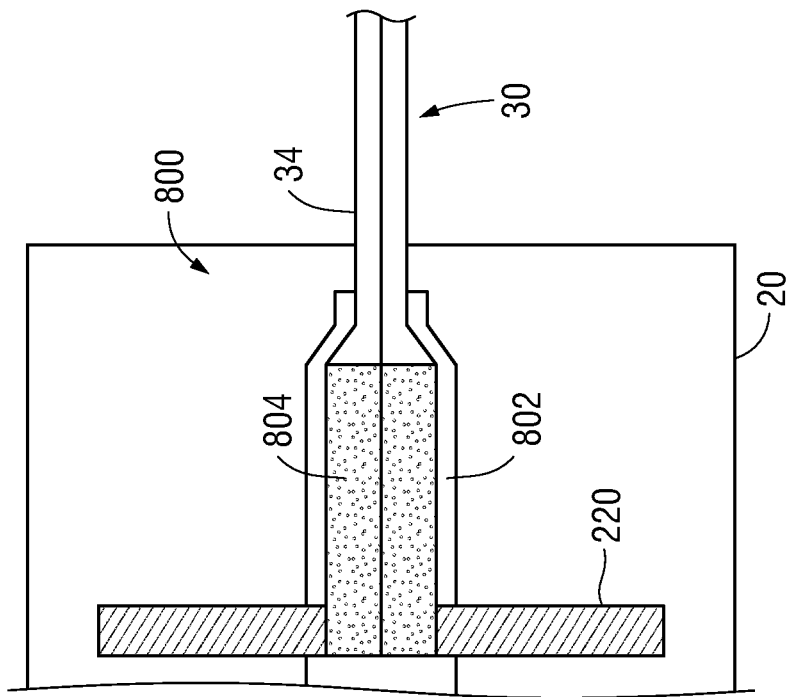
FIG. 8 is a longitudinal cross-sectional view of another proximal portion of a shaft configured for use with the surgical instrument of FIG. 1 including a seal in accordance with the present disclosure.

Referring to FIG. 8, another seal configuration 800 provided in accordance with the present disclosure is shown in use at location "A" (FIGS. 1, 2A-2C, and 6). More specifically, seal configuration 800 includes a connector shaft 802 including a seal 804 disposed therein. Connector shaft 802 is disposed within housing 20 and secured, e.g., welded or otherwise attached, to distal plate 220 of lead screw sub-assembly 210 (see FIGS. 2A-2C) and proximal segment 34 of shaft 30 to thereby secure proximal segment 34 of shaft 30 to distal plate 220. Connector shaft 802 defines a larger internal diameter as compared to proximal segment 34 of shaft 30. The relatively larger internal diameter of connector shaft 802 facilitates the manufacture of seal 804 and/or assembly of seal 704 within connector shaft 802. Further, upon assembly, seal 804 is substantially retained in position within connector shaft 802 proximal segment 34 of shaft 30 as distal plate 220 inhibits substantial proximal movement of seal 804 while the smaller diameter proximal segment 34 of shaft 30 inhibits substantial distal movement of seal 804. Seal 804 may be formed, inserted, assembled, and/or configured similarly as detailed above with respect to seal 704 (FIG. 7) or in any other suitable manner.

Figure 9A:
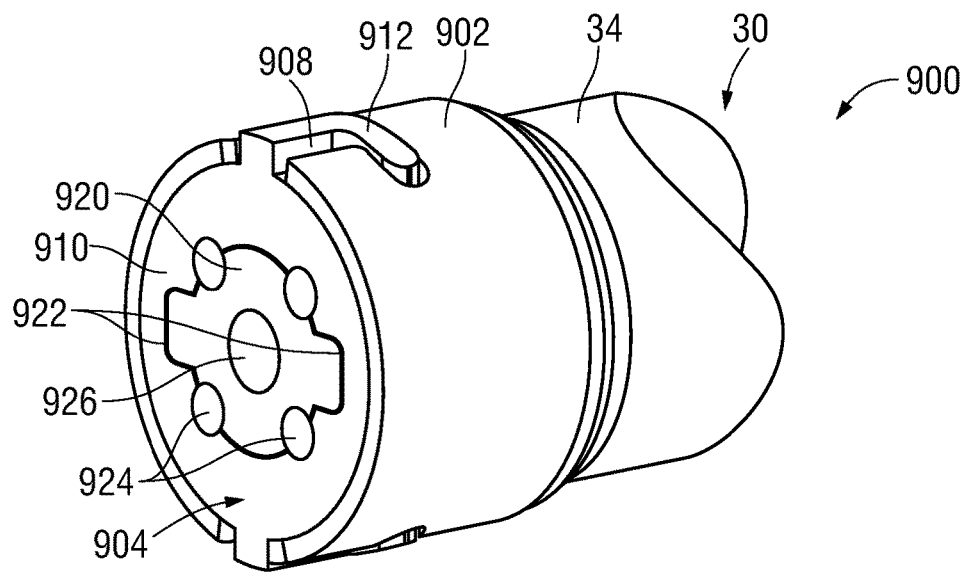
FIGS. 9A and 9B are perspective and exploded perspective views, respectively, of still another proximal portion of a shaft configured for use with the surgical instrument of FIG. 1 including a seal in accordance with the present disclosure.
Figure 9B:
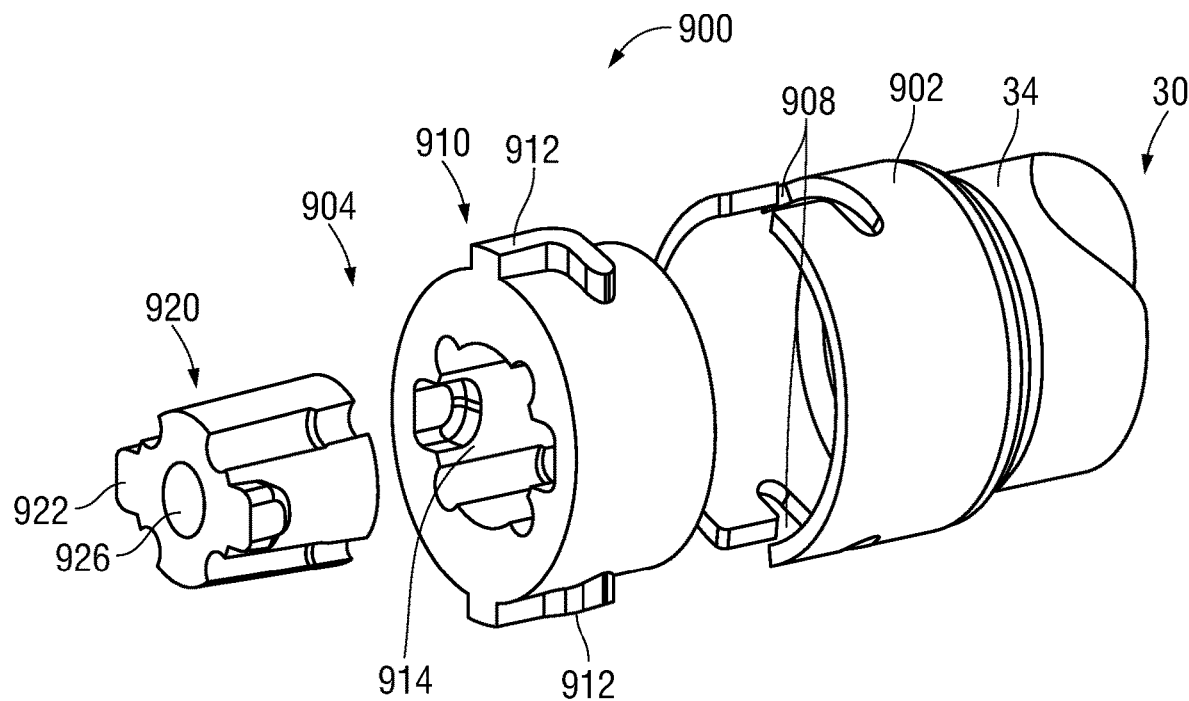

FIGS. 9A and 9B illustrate still another seal configuration 900 provided in accordance with the present disclosure for use at location "A" (FIGS. 1, 2A-2C, and 6) or any other suitable location. More specifically, seal configuration 900 includes an enlarged proximal end portion 902 of proximal segment 34 of shaft 30 and a two-part seal 904 disposed therein. Enlarged proximal end portion 902 is disposed within housing 20 (see FIGS. 4 and 5) and may be secured, e.g., welded or otherwise attached, to distal plate 220 of lead screw sub-assembly 210 (see FIGS. 2A-2C). Enlarged proximal end portion 902 defines a larger internal diameter as compared to the body of proximal segment 34 of shaft 30. The relatively larger internal diameter of enlarged proximal end portion 902 facilitates the manufacture of seal 904 and/or assembly of seal 904 within enlarged proximal end portion 902. Enlarged proximal end portion 902 includes one or more retention slots 908 defined therein, each defining an L-shaped configuration. Although two diametrically-opposed, L-shaped retention slots 908 are shown in FIG. 9B, other number and/or configuration of retention slots 908 are also contemplated such as, for example, T-shaped slots.

Two-part seal 904 includes an outer collar 910 and an inner plug 920. Outer collar 910 includes one or more retention protrusion 912 extending radially outwardly therefrom, each defining an L-shaped configuration. Although two diametrically-opposed, L-shaped protrusions 912 are shown in FIG. 9B, other number and/or configuration of retention protrusions 912 complementary to retention slots 908 are also contemplated. Retention protrusions 912 are configured for receipt within retention slots 908 to fixedly seat outer collar 910 within enlarged proximal end portion 902 in sealed relation against an inner annular surface thereof. Outer collar 910 further includes an irregular, e.g., non-circular, lumen 914 defined therethrough.

Inner plug 920 of seal 904 is configured for complementary receipt within irregular lumen 914 of outer collar 910. Outer collar 910 and inner plug 920, with inner plug 920 received within irregular lumen 914 of outer collar 910, define complementary features 922, e.g., protrusions and recesses, and/or other suitable features or configurations such that inner plug 920 is fixedly retained within outer collar 910 and forms a seal therewith (notwithstanding any defined passages therethrough). Outer collar 910 and inner plug 920 may also cooperate to define one or more radial lumens 924 therebetween and/or inner plug 920 may define a central lumen 926. Lumens 924, 926 are configured to establish a seal with actuation components extending therethrough, e.g., articulation cables 38 (FIGS. 1, 4, and 5), knife tube 62 (FIGS. 4 and 5), and lead wires 99 (FIG. 1).

Outer collar 910 and inner plug 920 of seal 904 may be formed from the same or different materials and are configured to cooperate to establish a seal within enlarged proximal end portion 902 and about the actuation components extending therethrough. Thus, seal 904 functions to inhibit the passage of fluids proximally across seal 904 while still enabling operation of the actuation components extending therethrough.

Turning to FIGS. 10-13, various seal configurations 1000, 1100, 1200, 1300 provided in accordance with the present disclosure are shown. Seal configurations 1000, 1100, 1200, 1300 may be utilized with or without an enlarged proximal end portion of proximal segment 34 of shaft 30 and include retention features defined on, within, or otherwise associated with a proximal end portion 1002, 1102, 1202, 1302 of proximal segment 34 of shaft 30 to facilitate maintaining the corresponding seals 1004, 1104, 1204, 1304 in sealing relation and substantially fixed position within proximal segment 34 of shaft 30. Seal configurations 1000, 1100, 1200, 1300 may be duplicated and/or used in combination with one another and, although described for use at location "A," may alternatively or additionally, to the extent consistent, be utilized at location "B" and/or any other suitable location(s) (see FIGS. 1, 2A-2C, and 6).

Figure 10:
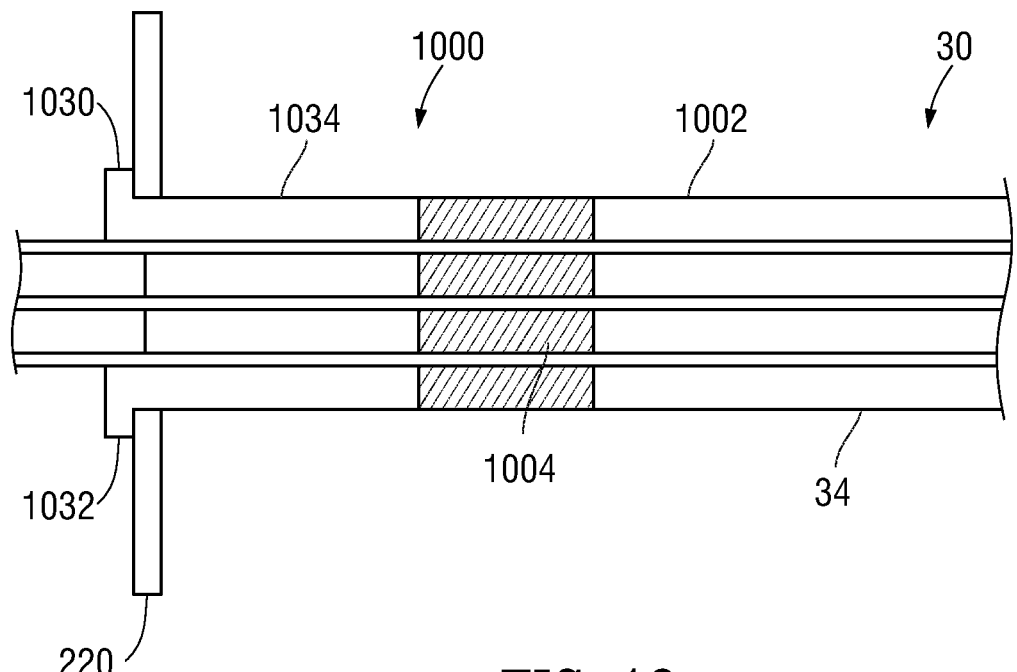
FIGS. 10-13 are longitudinal cross-sectional views of various proximal portions of shafts configured for use with the surgical instrument of FIG. 1 including seals in accordance with the present disclosure.

Seal configuration 1000 illustrated in FIG. 10 includes a lock ring 1030 having a proximal flange 1032 configured to proximally abut distal plate 220 of lead screw sub-assembly 210 (see FIGS. 2A-2C) and a distal body 1034 configured to extend through distal plate 220 and into proximal end portion 1002 of proximal segment 34 of shaft 30, e.g., in press-fit fashion. Distal body 1034 reduces the effective inner diameter of proximal end portion 1002, thus inhibiting proximal movement of seal 1004. Seal 1004 may be similar to seal 700 (FIG. 7) or any other suitable seal.

Figure 11:
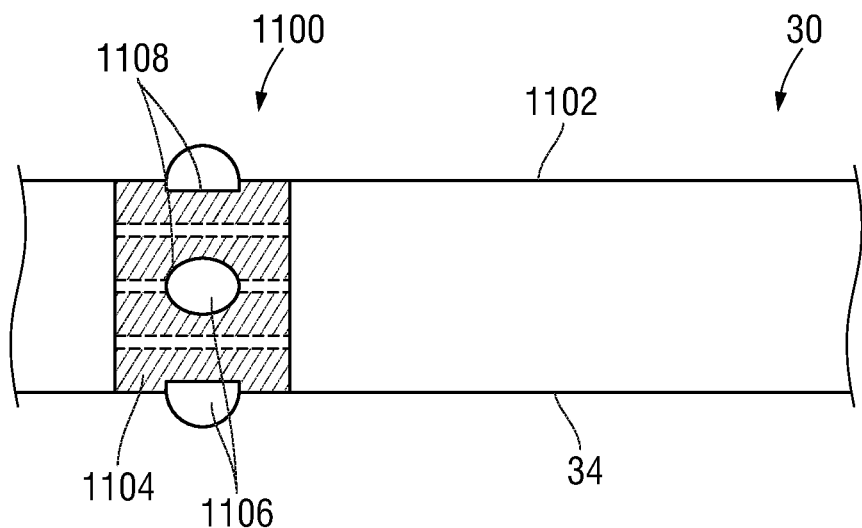

As illustrated in FIG. 11, seal configuration 1100 includes a plurality of protrusions 1106 disposed annularly about and extending radially outwardly from seal 1104 and a plurality of corresponding apertures 1108 defined annularly about proximal end portion 1102 of proximal segment 34 of shaft 30, although the opposite configuration or protrusions and apertures on both seal 1104 and proximal end portion 1102 are also contemplated. Upon insertion of seal 1104 into proximal end portion 1102, protrusions 1106 are compressed radially inwardly to enable insertion of seal 1104 into proximal end portion 1102. Upon alignment of protrusions 1106 with apertures 1108, protrusions 1106 are resiliently returned to extend through apertures 1108, thereby retaining seal 1104 in position within proximal end portion 1102. Seal 1104 may otherwise be similar to seal 700 (FIG. 7) or any other suitable seal.

Figure 12:
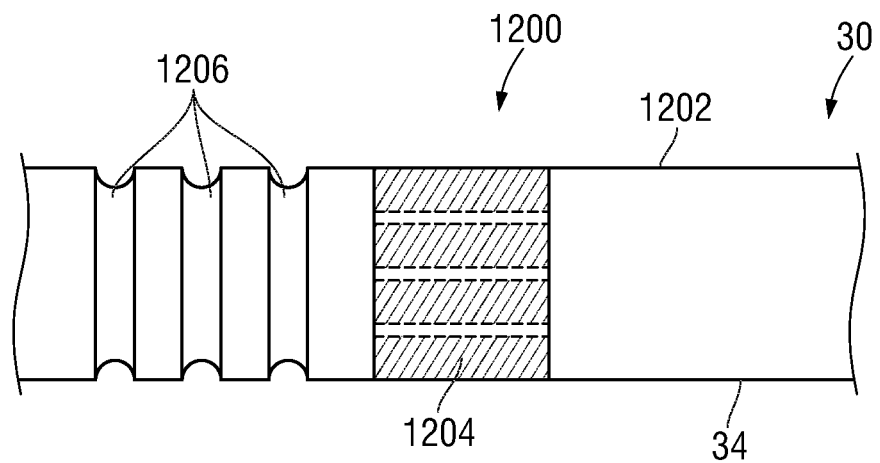

Seal configuration 1200 illustrated in FIG. 12 includes one or more annular ribs 1206 extending radially inwardly into proximal end portion 1202 of proximal segment 34 of shaft 30. Ribs 1206 may be formed via indenting the outer surface of proximal end portion 1202, adding additional material within proximal end portion 1202, or in any other suitable manner. Further, ribs 1206 may be disposed proximally, distally, or on both sides of seal 1204. Upon insertion of seal 1204 into proximal end portion 1202, seal 1204 is compressed radially inwardly to enable seal 1204 to pass through ribs 1206 to a position more-distal of ribs 1206. Once seal 1204 clears ribs 1206, seal 1204 is resiliently returned to seal against the inner surface proximal end portion 1202. The reduced effective diameter of proximal end portion 1202 provided by ribs 1206 inhibits seal 1204 from moving proximally. Seal 1204 may be similar to seal 700 (FIG. 7) or any other suitable seal.

Figure 13:
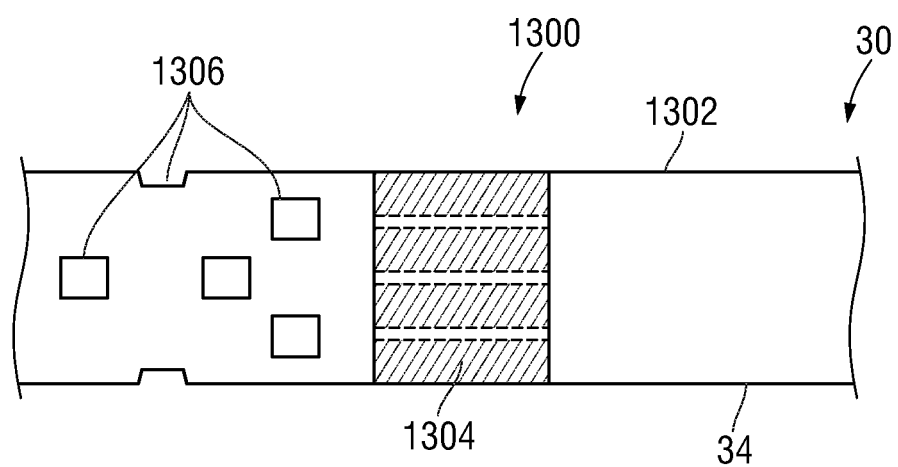

Illustrated in FIG. 13 is seal configuration 1300 which is similar to seal configuration 1200 (FIG. 12) except that, rather than ribs inhibiting proximal movement of the seal, seal configuration 1300 includes a plurality of radially and axially arranged protrusions 1306 protruding radially inwardly into the interior of proximal end portion 1302 to reduce the effective inner diameter thereof.

Figure 14:
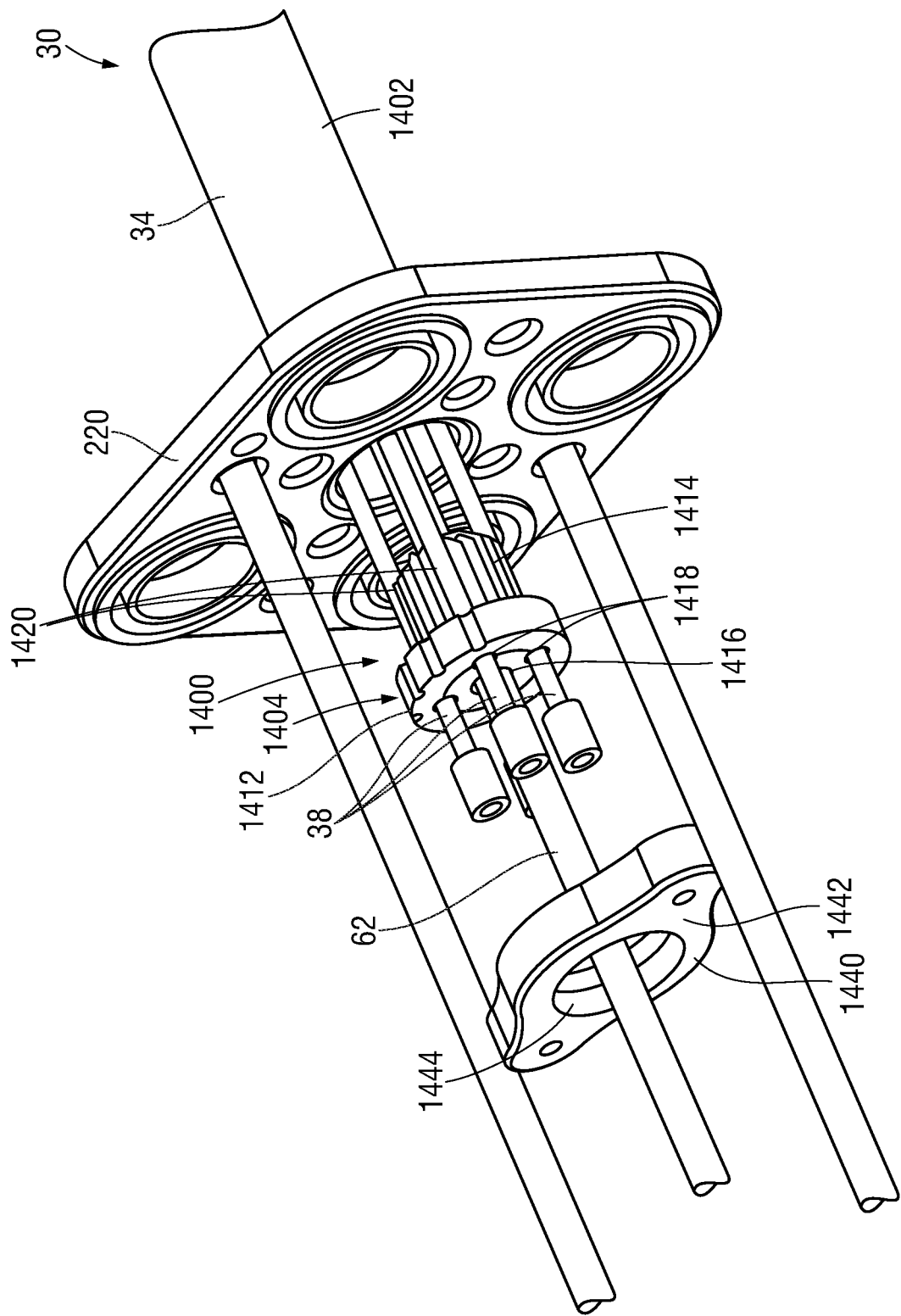
FIG. 14 is an exploded perspective view of a portion of an actuation assembly configured for use with the surgical instrument of FIG. 1, including a seal in accordance with the present disclosure.

Turning to FIG. 14, yet another seal configuration 1400 in accordance with the present disclosure is provided for use at location "A," location "C," a location therebetween, or any other suitable location(s) (see FIGS. 1, 2A-2C, and 6). Seal configuration 1400 includes a seal 1404 and a lock plate 1440. Seal 1404 includes a proximal flange 1412 configured to proximally abut distal plate 220 and a distal body 1414 configured to extend through distal plate 220 and into proximal end portion 1402 of proximal segment 34 of shaft 30. Seal 1404 may include one or more lumens 1416 extending completely therethrough, one or more apertures 1418 extending through proximal flange 1412, and/or one or more channels 1420 extending along distal body 1414 that individually or in cooperation sealingly engage the actuation components extending therethrough, e.g., articulation cables 38, knife tube 62, and lead wires 99 (FIG. 1). Slits defined within proximal flange 1412 and/or distal body 1414 provide sealable connections between the lumens 1416, apertures 1418, and/or exterior annular surfaces of proximal flange 1412 and/or distal body 1414 to facilitate the insertion and engagement of the actuation components therein. Such slits may likewise be used for similar purposes in other seal configurations detailed herein.

Lock plate 1440 includes a body 1442 defining one or more apertures 1444 that align with the lumens, 1416, apertures 1418, and channels 1420 of seal 1404 to enable passage of the actuation components, e.g., articulation cables 38, knife tube 62, and lead wires 99 (FIG. 1), therethrough. Lock plate 1440 is configured to proximally abut proximal flange 1412 of seal 1404 to at least partially compress proximal flange 1412 between lock plate 1440 and distal plate 220, thereby establishing a seal about the passage extending through distal plate 220 and shaft 30. Alternatively or additionally, any gap(s) may be filed with grease or other suitable material to establish the seal. Lock plate 1440 is secured in position relative to distal plate 220, this maintaining the seal, via screwing lock plate 1440 onto distal plate 220 and/or using any other suitable fasteners or engagement features. Distal body 1414 of seal 1404 may additionally or alternatively extend through distal plate 220 and into proximal end portion 1402 of proximal segment 34 of shaft 30 in sealing relation with an inner surface of proximal end portion 1402 to establish a seal therein.

Referring to FIGS. 15-17A, still yet other configurations 1500, 1600, 1700 are provided in accordance with the present disclosure configured for use at location "A" and/or any other suitable location(s) (see FIGS. 1, 2A-2C, and 6). Configurations 1500, 1600, 1700 may each include one or more portions 1501, 1601, 1701 of housing 20 that are sealed off, e.g., via a bulkhead 1503, 1603 or other suitable structure or combination of structures, to define a sealed volume within housing 20; in some configurations, the entirely of the interior of housing 20 defines the sealed volume. Although portions 1501, 1601, 1701 are illustrated at the distal end of housing 20, additional and/or alternative locations are also contemplated.

Figure 15:
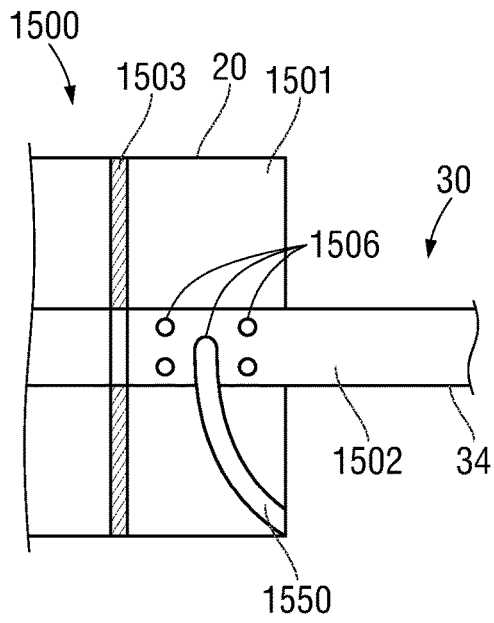
FIGS. 15, 16, and 17A are longitudinal cross-sectional views of distal portions of housings and proximal portions of shafts configured for use with the surgical instrument of FIG. 1 including various configurations for sealing, absorbing, and/or draining in accordance with the present disclosure.

With respect to configuration 1500 in FIG. 15, one or more apertures 1506 or other openings are defined through proximal end portion 1502 of proximal segment 34 of shaft 30 that fluidly communicate with the sealed volume defined by portion 1501. Thus, fluids traveling proximally through proximal segment 34 of shaft 30 and into housing 20 may exit proximal end portion 1502 and enter portion 1501 via apertures 1506. Alternatively or additionally, a drain tube 1550 connected to one of the apertures 1506 and/or in fluid communication with portion 1501 of housing 20 may be provide to enable drainage of such fluids. In such configuration, a fitting or other suitable connection (not shown) may be provided on housing 20 to enable connection of a drainage line (not shown).

Figure 16:
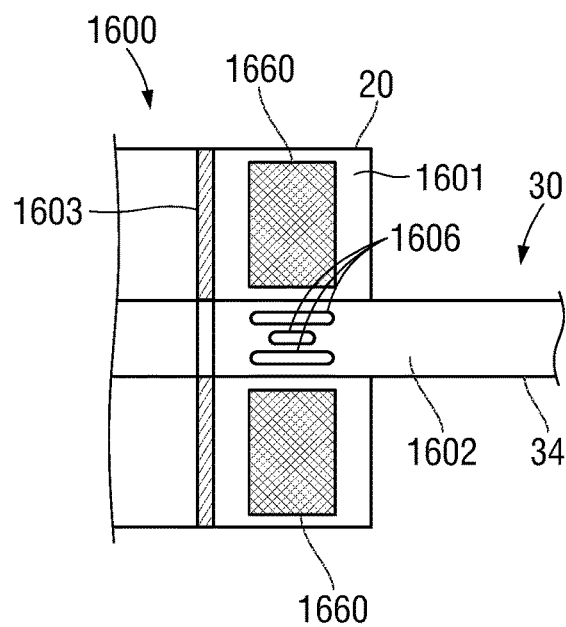

Configuration 1600 illustrated in FIG. 16 likewise includes one or more apertures 1606 or other openings are defined through proximal end portion 1602 of proximal segment 34 of shaft 30 that fluidly communicate with the sealed volume defined by portion 1601. Configuration 1600 difference from configuration 1500 (FIG. 15) in that, rather than providing a drain tube, configuration 1600 includes one or more sponges 1660 or other suitable fluid-absorbing materials disposed within portion 1601 so as to absorb fluids entering portion 1601 via apertures 1606.

Figure 17A:
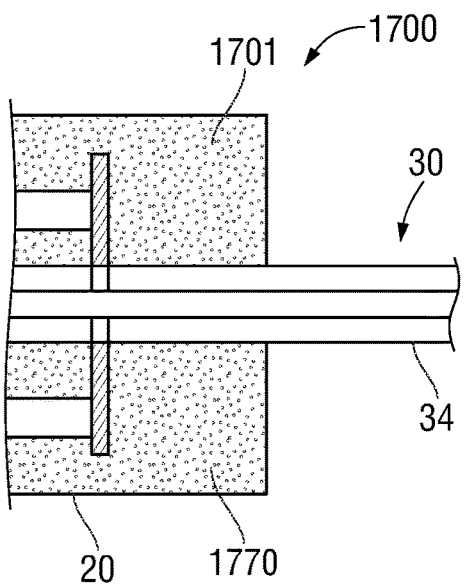
Figure 17B:
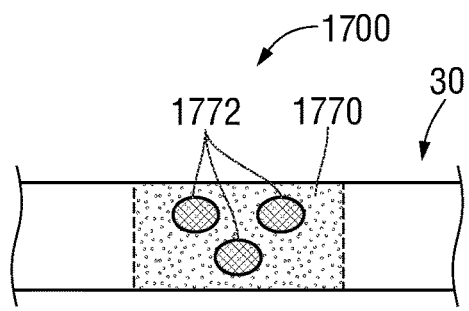
FIG. 17B is a longitudinal cross-sectional view of a portion of a shaft configured for use with the surgical instrument of FIG. 1 including still another seal in accordance with the present disclosure.

FIG. 17A illustrates a configuration 1700 wherein the portion 1701 of housing 20 or the entirety of housing 20 is filled with an injectable material 1770, e.g., a sealant material and/or absorbent material, to form a seal against passage fluids and/or to absorb fluids. The injectable material 1770 may be a foam, gel, grease, phase-change material, etc. As shown in FIG. 17B, in other configurations, apertures 1772 defined within shaft 30 (or other components) may be provide to enable injection of the injectable material 1770 to provide additional seals and/or absorbent areas, e.g., at locations "B" or "E" (see FIGS. 1, 2A-2C, and 6), e.g., sealing shaft 30 and the components extending therethrough.

Figure 18:
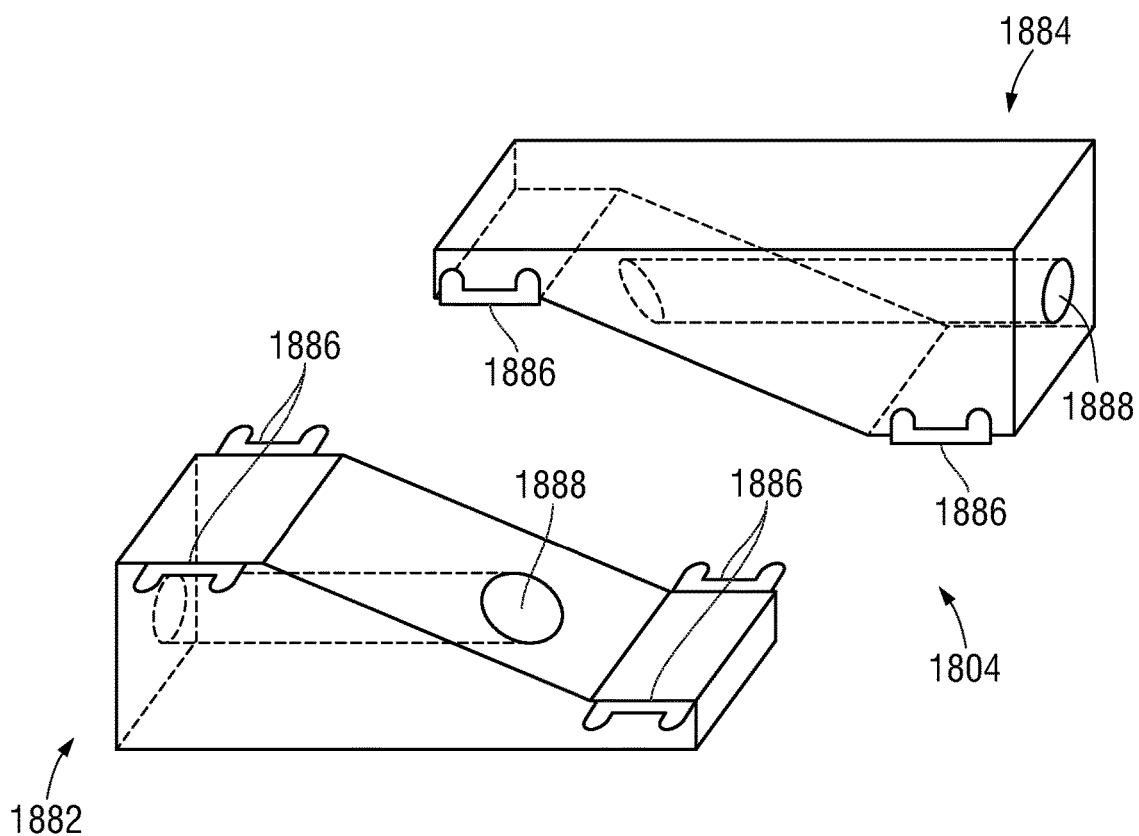
FIG. 18 is an exploded perspective view of another seal in accordance with the present disclosure.

Turning to FIG. 18, another seal 1804 provided in accordance with the present disclosure is configured for use at locations "A," "B," "E" (FIGS. 1, 2A-2C, and 6) and/or any other suitable location(s). Seal 1804 includes a pair of wedge seal members 1882, 1884. Wedge seal members 1882, 1884 may define complementary engagement features 1886, e.g., interlocking tabs, protrusion and apertures, etc., configured to engage one another to secure wedge seal members 1882, 1884 to one another. Each wedge seal member 1882, 1884 further defines one or more lumens 1888 extending therethrough that align with one another upon engagement of wedge seal members 1882, 1884. When wedge seal members 1882, 1884 are engaged with one another, seal 1804 may define a rectangular cross-sectional configuration, a circular cross-sectional configuration, or any other suitable configuration to enable sealing of seal 1804 within an area, e.g., within shaft 30 (FIG. 1). Lumens 1888 are configured to receive one or more actuation components, e.g., articulation cables 38 (FIGS. 1, 4, and 5), knife tube 62 (FIGS. 4 and 5), and lead wires 99 (FIG. 1), in sealing relation therewith while still enabling operation thereof.

In use with respect to shaft 30 (FIG. 1), for example, wedge seal member 1882 is inserted in a first direction, e.g., distally, through a portion of shaft 30 and about the one or more actuation components while wedge seal member 1884 is inserted in a second opposite direction, e.g., proximally, through a portion of shaft 30 and about the one or more actuation components until wedge seal members 1882, 1884 meet and engage one another via complementary engagement features 1886, thereby forming a seal within shaft 30 and about the one or more actuation components. Wedge seal members 1882, 1884 may be formed from the same or different materials including elastomeric materials or other suitable materials.

Figure 19:
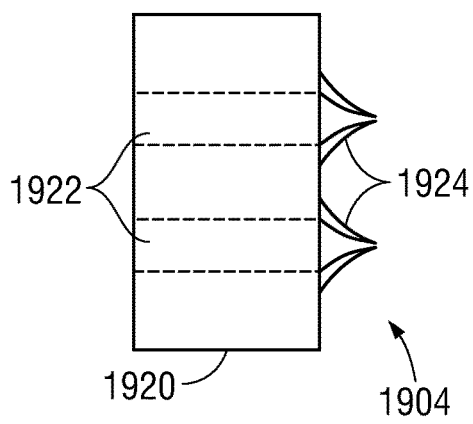
FIGS. 19 and 20 are side views of still other seals in accordance with the present disclosure.

Referring to FIG. 19, another seal 1904 provided in accordance with the present disclosure is configured for use at locations "A," "B," "E" (FIGS. 1, 2A-2C, and 6) and/or any other suitable location(s). Seal 1904 includes a seal body 1920. Seal body 1920 is configured to establish a seal against an inner surface of a structure, e.g., an inner surface of shaft 30 (FIG. 1). Seal body 1920 has one or more lumens 1922 extending therethrough. Each lumen 1922 defines a diameter equal to or larger than a diameter of the actuation component(s), e.g., articulation cables 38 (FIGS. 1, 4, and 5), knife tube 62 (FIGS. 4 and 5), and lead wires 99 (FIG. 1), configured for passage therethrough. A plurality of duckbill seals 1924 extend from either or both sides of seal body 1920 with each duckbill seal 1924 surrounding an end of one of the lumens 1922. Duckbill seals 1924 may be zero-closure seals or may close to a diameter less than the actuation component(s), e.g., articulation cables 38 (FIGS. 1, 4, and 5), knife tube 62 (FIGS. 4 and 5), and lead wires 99 (FIG. 1), configured for passage therethrough. In this manner, seal body 1920 seals against the outer structure, e.g., shaft 30, while duckbill seals 1924 seal about the inner structure(s), e.g., the actuation component(s). Duckbill seals 1924 may additionally or alternatively establish a seal about the actuation component(s) when there is a pressure differential across seal 1904, e.g., when shaft 30 (FIG. 1) is inserted into an insufflated body cavity.

Figure 20:
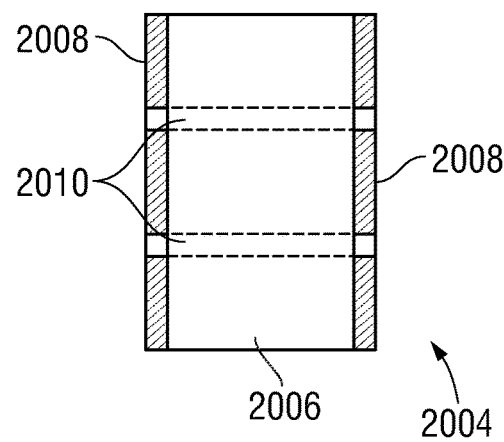

Turning to FIG. 20, another seal 2004 provided is configured for use at locations "A," "B," "E" (FIGS. 1, 2A-2C, and 6) and/or any other suitable location(s) and includes a compressible seal body 2006 captured between a pair of rigid plates 2008. Body 2006 and plates 2008 may cooperate to define lumens 2010 therethrough to enable passage of actuation components in sealed relation with seal body 2006. During assembly, seal body 2006 may be inserted into an outer structure, e.g., shaft 30, and/or about an inner structure, e.g., one or more actuation components, prior to positioning of plates 2008. Plates 2008 may then be positioned on either side of seal body 2006 and moved towards one another to axially compress seal body 2006, urging seal body 2006 to seal within the outer structure and/or about the inner structure. Plates 2008 may be retained in position via engagement with one another and/or the outer structure.

Figure 21:
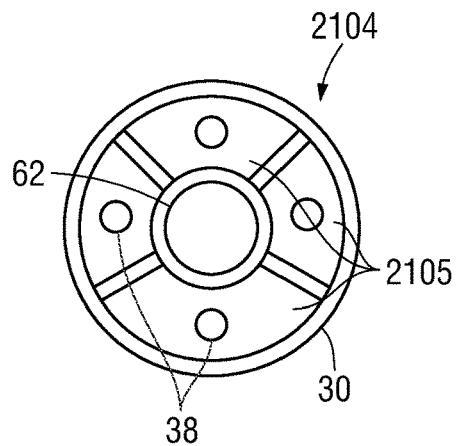
FIGS. 21 and 22 are transverse cross-sectional views of yet other seals in accordance with the present disclosure.

With reference to FIG. 21, still yet another seal 2104 is configured for use at locations "A," "B," "E" (FIGS. 1, 2A-2C, and 6) and/or any other suitable location(s). Seal 2104 includes a plurality of seal components 2105 each sealed about and disposed in fixed relation, e.g., via overmolding, relative to an actuation component, e.g., one of the articulation cables 38. Seal components 2105 cooperate to act as wipers that maintain a seal about an outer structure, e.g., shaft 30, and/or an inner structure, e.g., knife tube 62, even where relative translation therebetween occurs.

Figure 22:
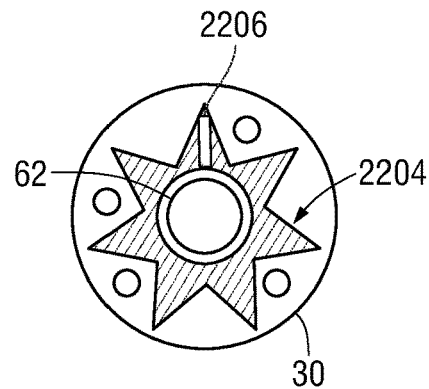

Referring to FIG. 22, an absorbent and/or seal member 2204 provided in accordance with the present disclosure for use at locations "A," "B," "E" (FIGS. 1, 2A-2C, and 6) and/or any other suitable location(s) is initially disposed in a contracted configuration. Member 2204 is disposed, e.g., sealingly disposed, about an inner actuation component, e.g., knife tube 62, and may define a slit 2206 to enable transverse insertion of member 2204 about knife tube 62. Member 2204 is configured for positioning within shaft 30 (or other suitable outer component) and is initially disposed in non-sealing relation therewith, occupying a relatively small volume within shaft 30. Slit 2206 may be a zero-closure slit. As fluids contact and are absorbed by member 2204, member 2204 expands to fill a relatively larger volume within shaft 30 and, in some configurations, when sufficiently saturated and expanded, established a seal therein.

Figure 23:
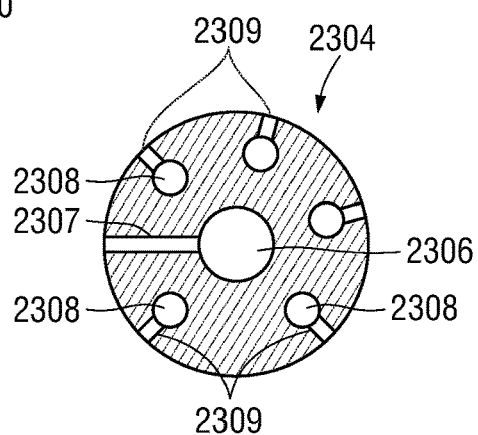
FIG. 23 is a transverse cross-sectional view of another seal in accordance with the present disclosure.

FIG. 23 illustrates another seal 2304 provided in accordance with the present disclosure for use at locations "A," "B," "E" (FIGS. 1, 2A-2C, and 6). For example, seal 2304 may be configured for positioning within an outer structure, e.g., shaft 30 (FIG. 1) to establish a seal about an inner surface thereof. Seal 2304 includes a central aperture 2306 and a plurality of radial apertures 2308. Apertures 2306, 2308 are configured to receive and sealingly engage actuation component(s), e.g., articulation cables 38 (FIGS. 1, 4, and 5), knife tube 62 (FIGS. 4 and 5), and lead wires 99 (FIG. 1). Each aperture 2306, 2308 includes a slit 2307, 2309, respectively, connecting the aperture 2306, 2308 with an outer annular periphery of seal 2304 such that each of the actuation components may be slid transversely through one of the slits 2307, 2309 and into sealing engagement within the corresponding aperture 2306, 2308, respectively. Slits 2307, 2309 may be zero-closure slits.

Figure 24:
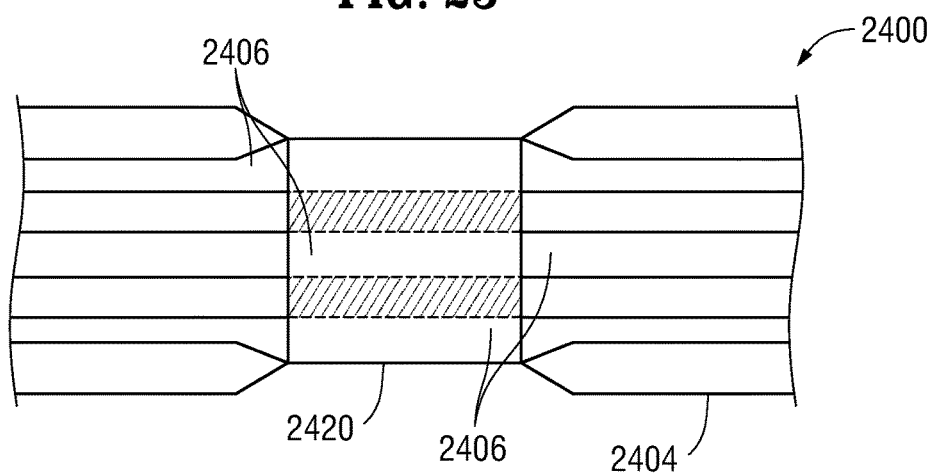
FIGS. 24 and 25 are longitudinal cross-sectional views of portion of shafts configured for use with the surgical instrument of FIG. 1 including other seals in accordance with the present disclosure.

As shown in FIG. 24, another seal configuration 2400 is provided including a seal member 2404 defining one or more apertures 2406 extending longitudinally therethrough. Seal configuration 2400 may be used at locations "A," "B," "E" (FIGS. 1, 2A-2C, and 6) and/or any other suitable location(s). Seal member 2404 is configured for insertion into a structure and to establish a seal against an inner surface of the structure, e.g., an inner surface of shaft 30 (FIG. 1). The one or more apertures 2406 may be configured to receive an actuation component(s), e.g., articulation cables 38 (FIGS. 1, 4, and 5), knife tube 62 (FIGS. 4 and 5), and lead wires 99 (FIG. 1). A portion of seal member 2404 is compressed radially inwardly, e.g., via a band 2420 disposed about a portion of seal member 2404, such that the one or more apertures 2406 are collapsed and seal member 2404 establishes a sealed engagement with the actuation component(s). While the compressed portion of seal member 2404 is no longer sufficiently expanded to seal shaft 30 (FIG. 1), other portions of seal member 2404 or another seal may be utilized to seal shaft 30 (FIG. 1).

Figure 25:
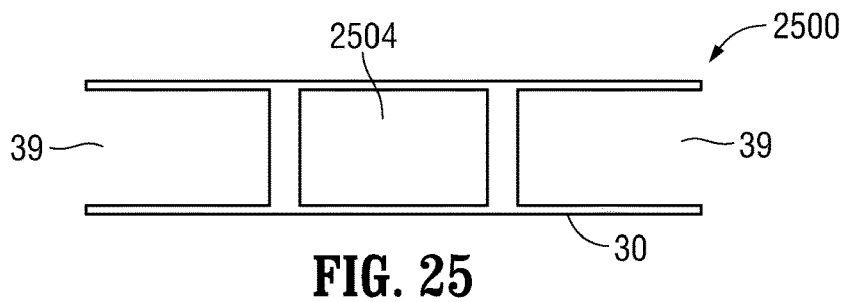

FIG. 25 provides a seal configuration 2500 including a seal member 2504 similar to seal member 2404 (FIG. 24) except that, rather than radial inward compression, seal member 2504 may be configured to compress axially inwardly from opposed ends, e.g., via compression of seal member 2504 between two guide structures 39 disposed within shaft 30, to establish a seal within shaft 30 and/or about actuation component(s). Alternatively, seal member 2504 may be configured to any other seal detailed herein, e.g., seal 2304 (FIG. 2,) and retained in substantially fixed position within shaft 30 between the guide structures 39 (with or without compression).

Turning to FIGS. 26A and 26B, as noted above, one or more seals may be provided at location "C" at or near proximal end portions of knife assembly 60, knife drive assembly 300, and/or jaw drive assembly 400 (see FIGS. 2A-2C). More specifically, a seal 2604 may be provided to seal the annular area between knife drive lead screw 340 (and/or knife tube 62) and jaw drive rod 484.

Knife drive lead screw 340 may include a pair of diametrically opposed T-slots 2622 defined within an unthreaded proximal sleeve portion 2620 thereof. Seal 2604 may define a pair of diametrically opposed T-protrusions 2624 extending therefrom and configured for complementary engagement within the T-slots 2622 to engage seal 2604 with knife drive lead screw 340. Seal 2604 functions as a cap to sealingly enclose the open proximal ends of knife drive lead screw 340 and knife tube 62 disposed therein, with the exception of an aperture 2626 defined through a proximal wall thereof that sealingly receives jaw drive rod 484. Thus, fluids travelling proximally through knife tube 62 are inhibited from passing proximally beyond seal 2604.

FIGS. 27 and 28 illustrate alternative sealing arrangements for sealing between an inner component, e.g., jaw drive rod 484, and an outer component, e.g., knife tube 62 or knife drive lead screw 340, such as, for example, at location "C" at or near proximal end portions of knife assembly 60, knife drive assembly 300, and/or jaw drive assembly 400 (see FIGS. 2A-2C). An end of the outer component 62, 340 is formed with an internal annular pocket 2702, 2802 surrounding the lumen 2701, 2801 extending therethrough, e.g., via machining. The pocket 2702, 2802 may be semi-circular as shown with respect to pocket 2702, may be V-shaped as shown with respect to pocket 2802, or may define any other suitable configuration that enables capture of an O-ring 2706, 2806 therein. O-rings 2706, 2806 protrude into lumens 2701, 2801, respectively, to sealingly engage the inner component, e.g., jaw drive rod 484 extending through lumen 2701, 2801.

Figure 29A:
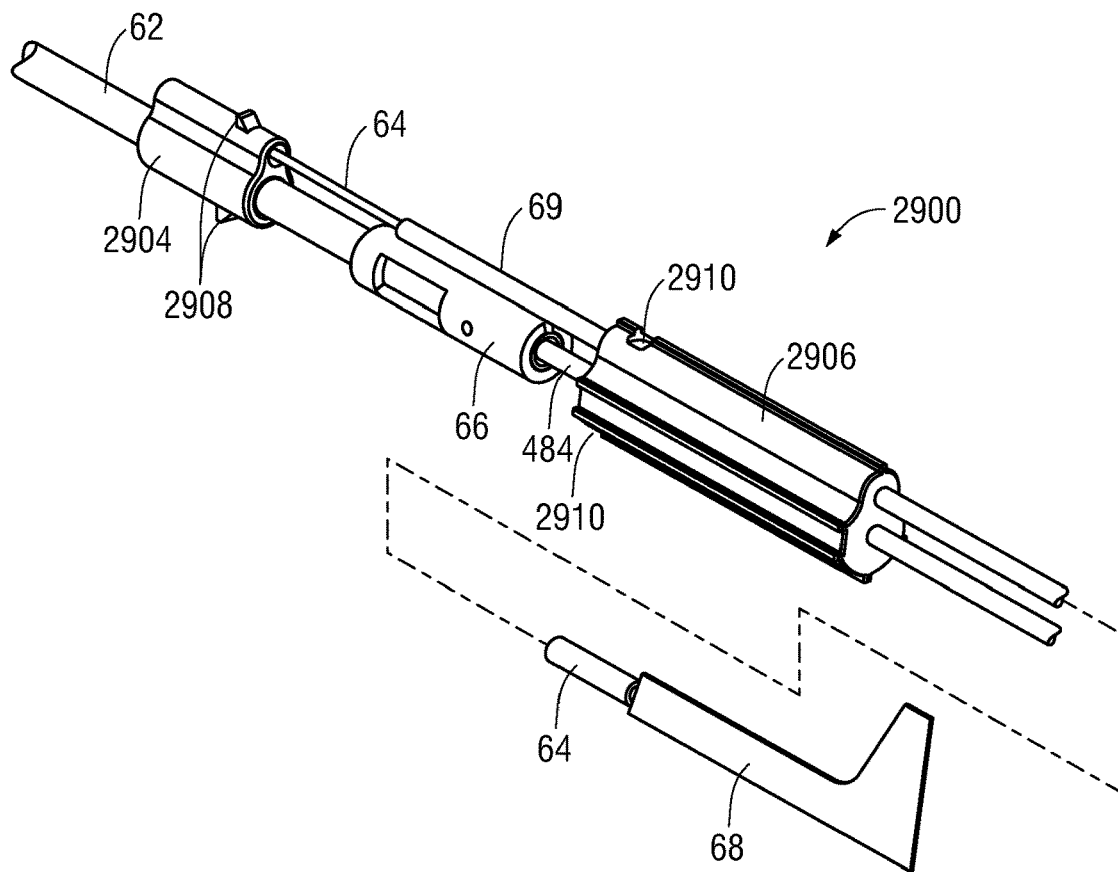
FIGS. 29A and 29B are exploded perspective and perspective views, respectively, of a distal portion of a knife assembly configured for use with the surgical instrument of FIG. 1 including still yet another seal in accordance with the present disclosure.
Figure 29B:
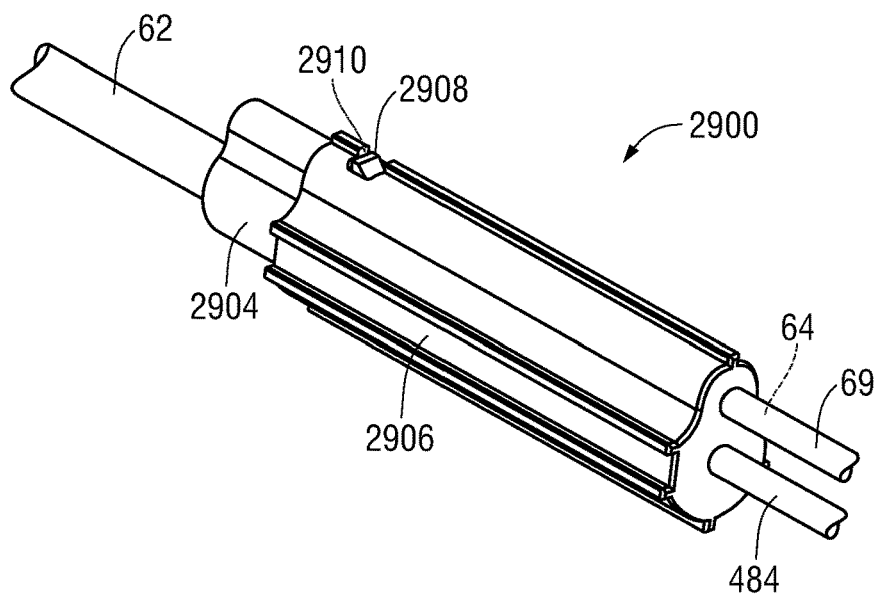

With reference to FIGS. 29A and 29B, a seal configuration 2900 is provided for establishing a seal at location "D," at or near distal end portions of knife assembly 60 and/or jaw drive assembly 400, although other locations are also contemplated (see FIGS. 1-6). More specifically, by sealing the open distal end of knife tube 62 about jaw drive rod 484 extending therefrom with seal configuration 2900, fluids are inhibited from entering and traveling proximally through knife tube 62.

Referring also reference to FIG. 1, momentarily, knife tube 62 extends through housing 20 and proximal segment 34 of shaft 30 to a position proximally adjacent articulating section 36 of shaft 30 (see FIG. 1) wherein intermediate elongated collar 66 is engaged about the distal end portion of knife tube 62. Distal knife rod 64 is engaged to intermediate elongated collar 66, e.g., via a crimp tube 69, in an offset position and extends distally therefrom through articulating section 36 of shaft 30 to end effector assembly 40 (see FIG. 1) wherein knife blade 68 is engaged to distal knife rod 64, distally of articulating section 36 of shaft 30. Distal knife rod 64 is flexible and/or includes one or more joints or articulating portions to permit articulation of articulating section 36 of shaft 30 with distal knife rod 64 extending therethrough. Jaw drive rod 484 extends through and distally from knife tube 62, through articulating section 36 of shaft 30 to end effector assembly 40 (see FIG. 1) wherein jaw drive rod 484 operably couples with cam-slot assembly 52 including to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) in response to translation of jaw drive rod 484. The offset engagement of distal knife rod 64 with intermediate collar 66 allows jaw drive rod 484 to extend distally from knife tube 62 to end effector assembly 40. Jaw drive rod 484 is flexible and/or includes one or more joints or articulating portions to permit articulation of articulating section 36 of shaft 30 with jaw drive rod 484 extending therethrough.

Referring again to FIGS. 29A and 29B, seal configuration 2900 includes a proximal seal member 2904 and a distal seal member 2906. Proximal seal 2904 is disposed about knife tube 62 proximally of intermediate elongated collar 66 and may also receive a proximal end portion of distal knife rod 64 therein. Distal seal 2906 is disposed about crimp tube 69 (which includes distal knife rod 64 extending therethrough) or directly about knife rod 64 (for example, in configurations where crimp tube 69 is omitted or otherwise positioned). Distal seal 2906 is also disposed about jaw drive rod 484 and is positioned distally of intermediate elongated collar 66.

Proximal and distal seals 2904, 2906 are configured to slide towards one another and about intermediate elongated collar 66 to a partially-overlapping condition wherein one of the seals, e.g., proximal seal 2904, is partially received within the other seal, e.g., distal seal 2906. Further, proximal and distal seals 2904, 2906 include complementary engagement features, e.g., lock tabs 2908 extending from the inner seal, e.g., proximal seal 2904, and lock apertures 2910 defined within the outer seal, e.g., distal seal 2906. In this manner, as proximal and distal seals 2904, 2906 are moved to the partially-overlapping condition, lock tabs 2908 are engaged within lock apertures 2910 to second proximal and distal seals 2904, 2906 with one another, collectively establishing a seal about intermediate elongated collar 66, the open distal end of knife tube 62, and jaw drive rod 484. Seal configuration 2900 may move together with knife tube 62 and/or may allow translation of jaw drive rod 484 relative thereto. Further, proximal and distal seals 2904, 2906 may be formed from the same or different materials.

Figure 30A:
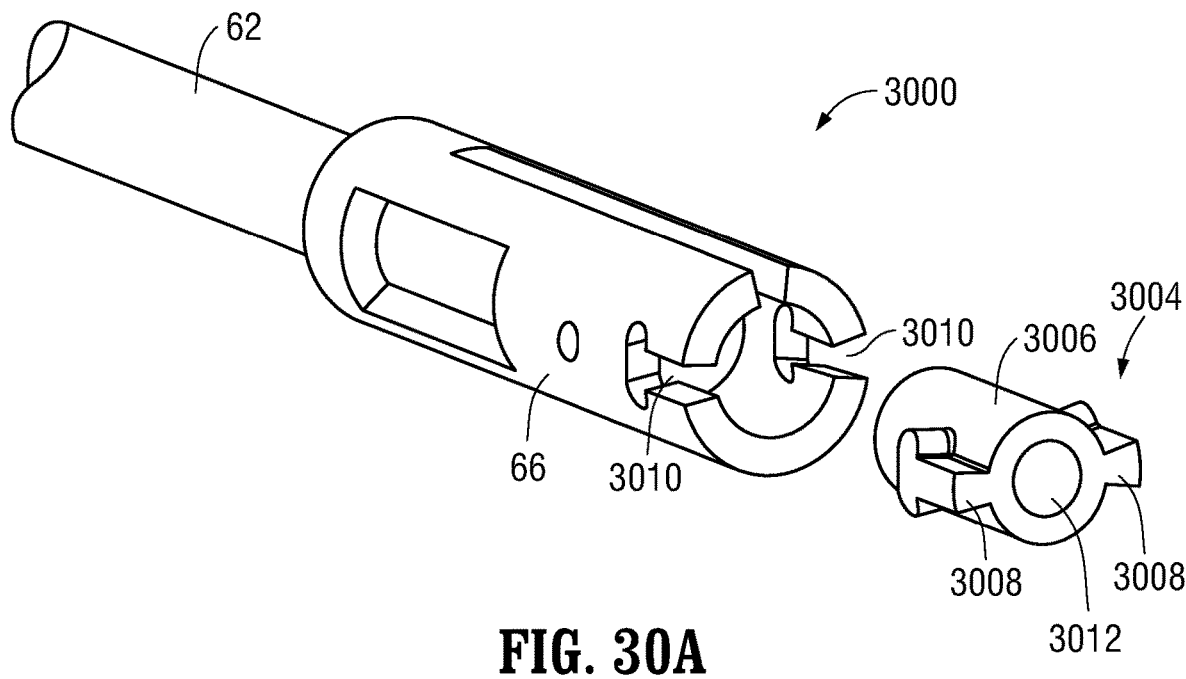
FIGS. 30A and 30B are exploded perspective and perspective views, respectively, of a portion of another knife assembly configured for use with the surgical instrument of FIG. 1 including a seal in accordance with the present disclosure.
Figure 30B:
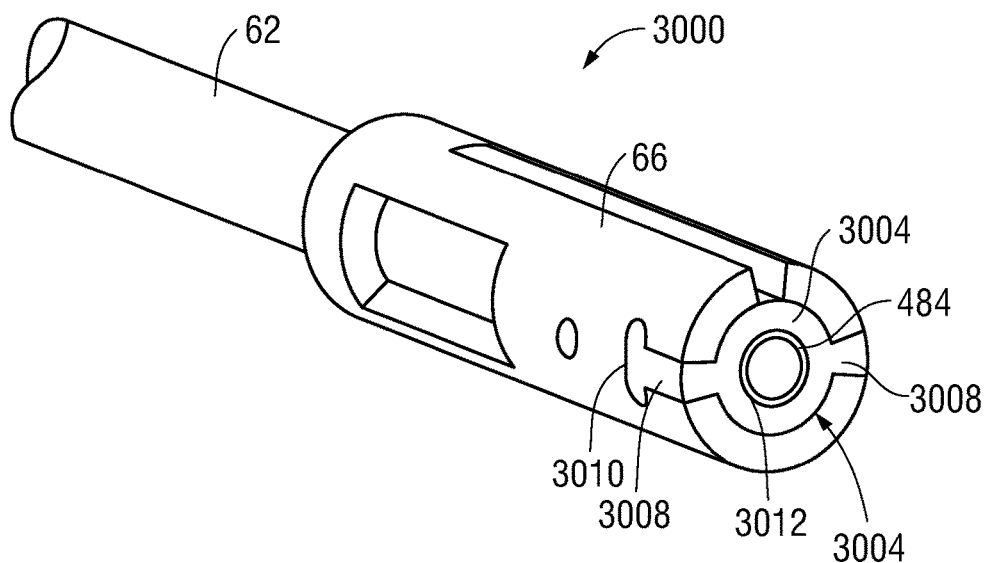

FIGS. 30A and 30B illustrate another seal configuration 3000 provided for establishing a seal at location "D," at or near distal end portions of knife assembly 60 and/or jaw drive assembly 400, although other locations are also contemplated (see FIGS. 1-6). Seal configuration 3000 is configured to seal the annular area defined between the open distal end of intermediate elongated collar 66 (and/or the open distal end of knife tube 62) and jaw drive rod 484.

Seal configuration 3000 includes a plug 3004 including a body 3006 configured to establish a seal about the inner surface of intermediate elongated collar 66 when inserted therein. Plug 3004 further includes a pair of diametrically opposed wings 3008 each defining a T-shaped configuration. Wings 3008 are configured for receipt within complementary diametrically opposed T-shaped slots 3010 defined within a distal end portion of intermediate elongated collar 66. Plug 3004 is inserted into intermediate elongated collar 66 such that body 3006 seals against the inner surface of intermediate elongated collar 66 while wings 3008 are engaged within slots 3010 to fixedly retain plug 3004 in sealing engagement within intermediate elongated collar 66. Plug 3004 further includes a central lumen 3012 extending therethrough that is configured to sealingly engage jaw drive rod 484 (FIG. 30B) while still allowing relative translation thereof. Plug 3004 may be formed from an elastomeric material or other suitable material.

Figure 31A:
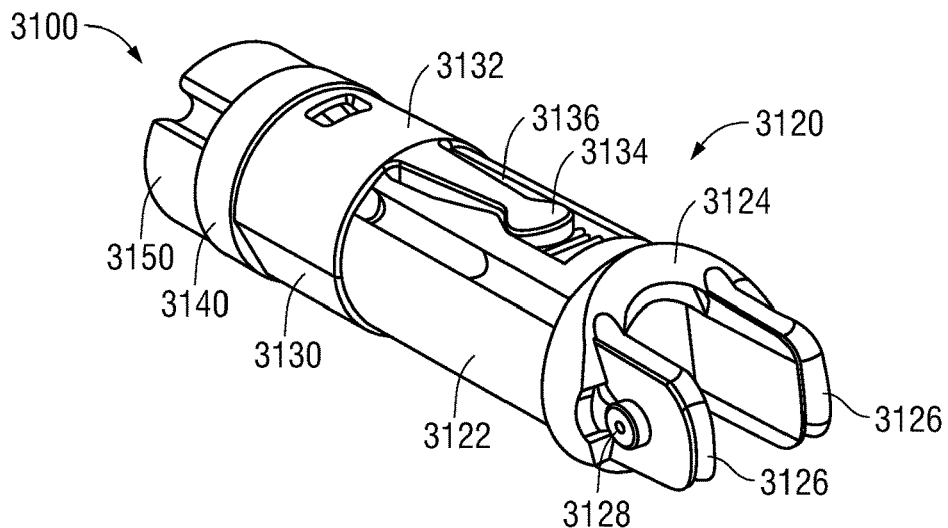
FIGS. 31A-31C are perspective, longitudinal cross-sectional, and end views respectively, of a portion of an articulating section configured for use with the surgical instrument of FIG. 1 including yet another seal in accordance with the present disclosure.

Turning to FIGS. 31A-13C, another seal configuration 3100 provided for establishing a seal at location "E," at or near articulating section 36 of shaft 30 (see also FIG. 1) is shown. Shaft 30, more specifically, includes articulating section 36 having one or more articulating components 37 (see FIG. 1). For example, one of the articulating components 37 (FIG. 1) may be a proximal link 3120 including a proximal body portion 3122, a distal face 3124 disposed at a distal end of proximal body portion 3122, and a pair of spaced-apart pivot flags 3126 extending distally from distal face 3124. Pivot flags 3126 include bosses 3128 to enable pivotable connection of proximal link 3120 with another articulating component 37 of articulating section 36 of shaft 30 (see FIG. 1). Proximal body portion 3122 may be configured for insertion into proximal segment 34 of shaft 30 with distal face 3124 abutting the open distal end of proximal segment 34 of shaft 30 (see FIG. 1).

Figure 31B:
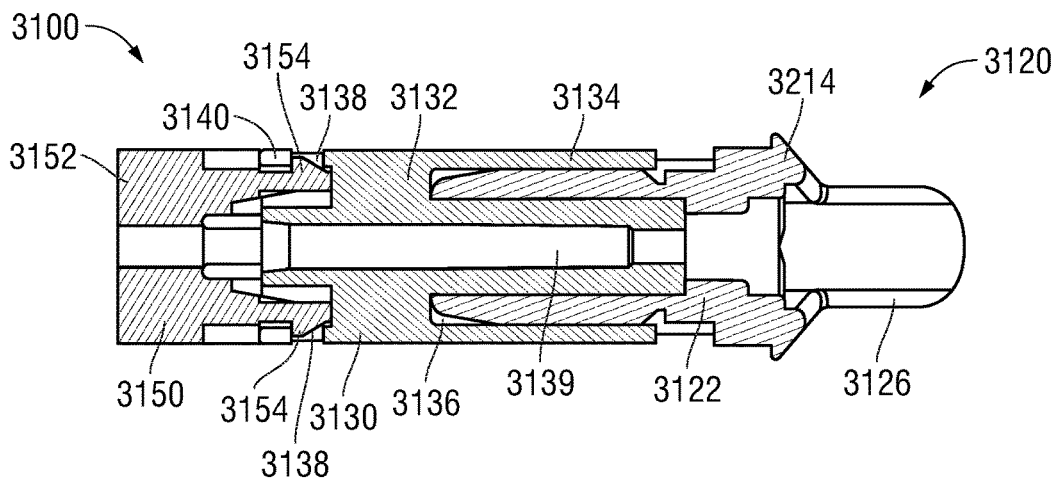
Figure 31C:
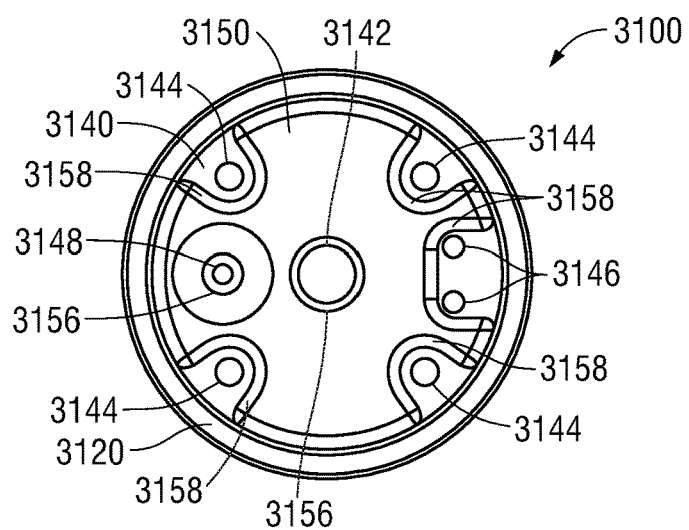

Continuing with reference to FIGS. 31A-31C, seal configuration 3100 includes a plug 3130, a seal ring 3140, and a clip 3150. Seal ring 3140 may be formed an elastomeric or other suitable material; plug 3130 and clip 3150 may be formed from elastomeric materials or from more rigid materials. Plug 3130 includes a base 3132 configured to proximally abut proximal body portion 3122 of proximal link 3120 and a pair of opposed arms 3134 extending distally from base 3132. Arms 3134 are configured for engagement within corresponding slots 3136 defined within proximal body portion 3122 of proximal link 3120. Seal ring 3140 is configured to proximally abut base 3132 of plug 3130 and clip 3150 includes a base 3152 configured to proximally abut seal ring 3140 and arms 3154 extending through seal ring 3150 and configured to engage, e.g., in snap-fit manner, slots 3138 of base 3132 of plug 3130 to thereby secure seal 3130 and clip 3150 with one another with seal ring 3140 disposed therebetween.

In the assembled condition, plug 3130, seal ring 3140, and clip 3150 cooperate with one another and proximal body portion 3122 of proximal link 3120 to establish a seal within the inner surface of proximal segment 34 of shaft 30 (see FIG. 1), e.g., via an outer annular surface of seal ring 3140, and to seal and guide the actuation components extending through proximal segment 34 of shaft 30 (see FIG. 1). More specifically, seal ring 3140 defines: a central aperture 3142 configured to sealingly receive jaw drive rod 484 (FIG. 2C); a plurality, e.g., four (4), radially-arranged apertures 3144 configured to sealingly receive articulation cables 38 (FIG. 1); a pair of adjacent apertures 3146 configured to sealingly receive the lead wires 99 (FIG. 1); and an offset aperture 3148 configured to sealingly receive distal knife rod 64 or crimp tube 69 disposed thereabout (see FIG. 29A). Clip 3150 may define apertures 3156 and/or cut-outs 3158 to provide access to the various apertures 3142-3148 defined through seal ring 3140. Plug 3130 may likewise include passages 3139, e.g., apertures and/or channels, for passage of the actuation components therethrough.

Figure 32:
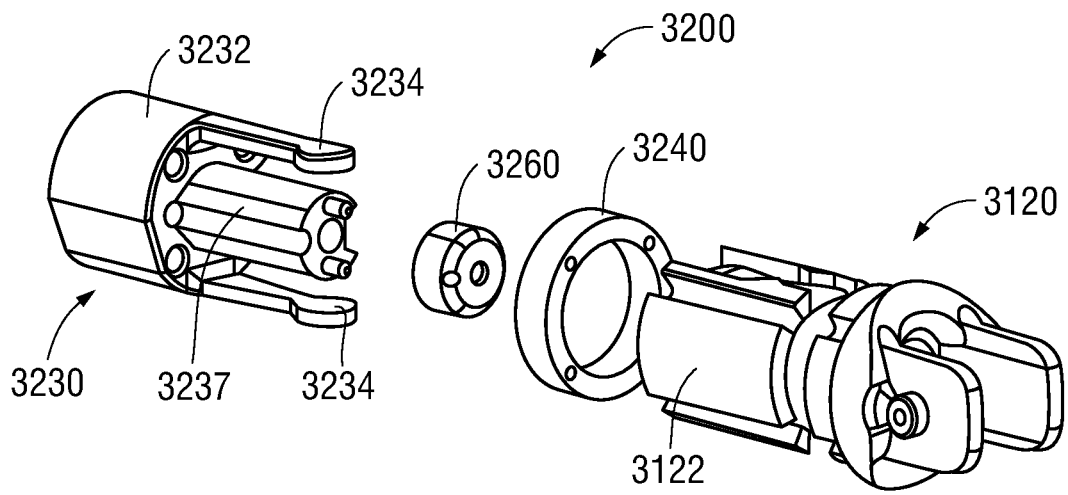
FIG. 32 is an exploded perspective view of another portion of an articulating section configured for use with the surgical instrument of FIG. 1 including a seal.

FIG. 32 illustrates still another seal configuration 3200 similar to seal configuration 3100 (FIGS. 31A-31C) and configured for operable engagement with proximal body portion 3122 of proximal link 3120 to establish a seal at location "E," at or near articulating section 36 of shaft 30 (see also FIG. 1). Seal configuration 3200 includes an engagement plug 3230, an outer seal ring 3240, and an inner seal plug 3260. Seal ring 3240 and seal plug 3260 may be formed from elastomeric or other suitable materials; engagement plug 3230 may be formed from an elastomeric material or from a more rigid material. Engagement plug 3230 includes a base 3232, a pair of opposed arms 3234 extending distally from base 3232, and a central cylinder 3237 extending distally from base 3232 between arms 3234. Outer seal ring 3240 is configured for positioning about central cylinder 3237 and between arms 3234 while inner seal plug 3260 is configured for distally abutting a distal end portion of central cylinder 3237. Engagement plug 3230 is configured to engage proximal body portion 3122 of proximal link 3120, e.g., via engagement of arms 3234 within slots similarly as detailed above with respect to seal configuration 3100 (FIGS. 31A-31C), with seal ring 3240 disposed therebetween in sealing engagement therewith, and with central cylinder 3237 and seal plug 3260 extending into proximal body portion 3122 of proximal link 3120 in sealing engagement therewith to form a seal against an inner surface of proximal link 3120. In use, outer seal ring 3240 establishes a seal within the inner surface of proximal segment 34 of shaft 30 (see FIG. 1) and seals about articulation cables 38 (FIG. 1) while inner seal plug 3260 seals about jaw drive rod 484 (FIG. 2C), the lead wires 99 (FIG. 1), and distal knife rod 64 (see FIG. 29A).

Figure 33:
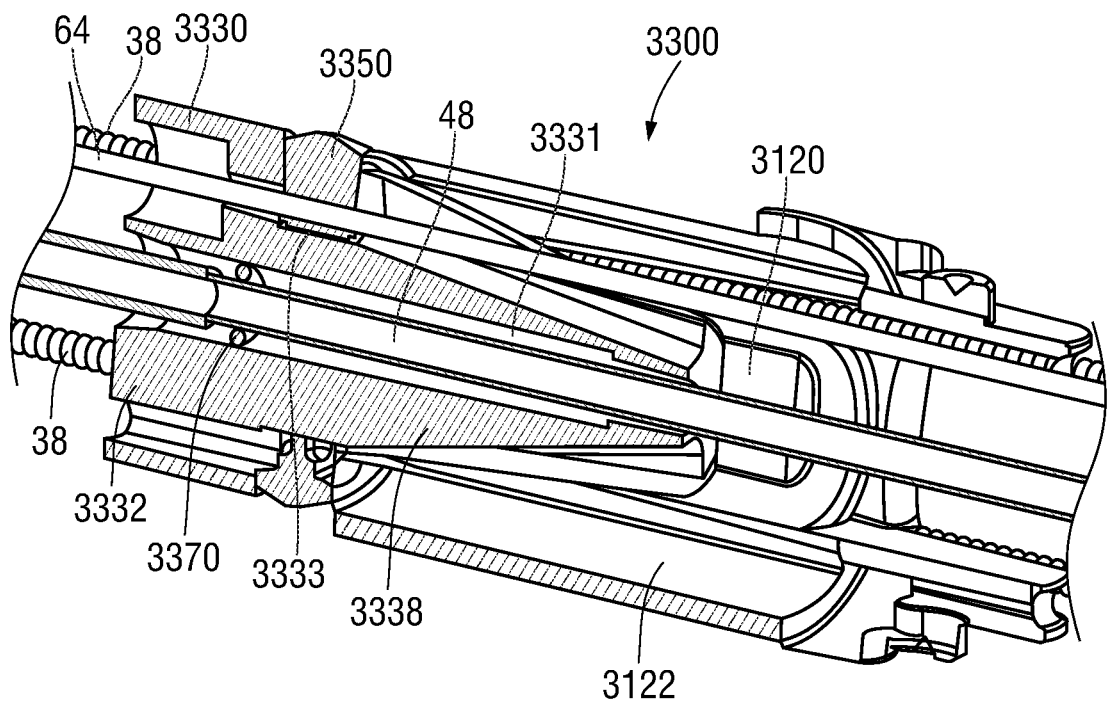
FIG. 33 is a longitudinal cross-sectional view of another portion of an articulating section configured for use with the surgical instrument of FIG. 1 including still another seal in accordance with the present disclosure.

Referring to FIG. 33, still another seal configuration 3300 similar to seal configurations 3100, 3200 (FIGS. 31A-31C and 32, respectively) configured for operable engagement with proximal body portion 3122 of proximal link 3120 to establish a seal at location "E," at or near articulating section 36 of shaft 30 (see also FIG. 1), is provided.

Seal configuration 3300 includes a plug 3330, an outer seal ring 3350, and an O-ring seal 3370. Plug 3330 includes a base 3332 and a conical body 3338 extending distally from base 3332. Conical body 3338 is configured for insertion into proximal body portion 3122 of proximal link 3120. Plug 3330 may be configured to engage proximal body portion 3122 in any suitable manner, e.g., press-fit, via arm and slot engagement, etc. Outer seal ring 3350 is configured for engagement within a slot 3333 defined within plug 3330 between base 3332 and conical body 3338 thereof. Outer seal ring 3350 protrudes radially outwardly from plug 3330 and proximal body portion 3122 of proximal link 3120 to enable formation of seal within the inner surface of proximal segment 34 of shaft 30 (see FIG. 1). Outer seal ring 3350 further defines radial lumens to sealingly engage articulation cables 38 and distal knife rod 64 or crimp tube 69 (see FIG. 29A). O-ring seal 3370 is disposed within central lumen 3331 of plug and is configured to seal jaw drive rod 484.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A robotic surgical instrument, comprising:
a housing;
a shaft extending distally from the housing and including a proximal segment, a distal segment, and an articulating portion interconnecting the proximal and distal segments, the articulating portion including a proximal link having a proximal body portion configured for at least partial receipt within the proximal segment of the shaft to define an annular space between an outer annular surface of the proximal body portion of the proximal link and an interior annular surface of the proximal segment of the shaft, the proximal link further including a distal pivoting portion configured to pivotably couple to a more-distal link of the articulating portion;
an end effector assembly coupled to the distal segment of the shaft and extending distally therefrom;
a plurality of actuation components extending through at least a portion of the shaft to operably couple to at least one of: the end effector assembly, the articulating portion, or the distal segment to enable selective actuation of the end effector assembly; and
a seal configuration operably associated with the proximal body portion of the proximal link of the articulating portion of the shaft to establish seals within the annular space, about each actuation component of the plurality of actuation components, and within the proximal body portion of the proximal link to inhibit fluid communication proximally into the proximal segment of the shaft, the seal configuration including a plug, a seal ring, and a clip arranged concentrically relative to one another, wherein the clip includes a base and first and second arms, the base of the clip and the plug disposed on opposing ends of the seal ring, and wherein the first and second arms of the clip extend through the seal ring to engage the plug, thereby securing the clip relative to the plug with the seal ring disposed therebetween.

2. The robotic surgical instrument according to claim 1, wherein the plurality of actuation components includes at least two of: a plurality of articulation cables; one or more electrical lead wires; a drive bar; or a drive tube.

3. The robotic surgical instrument according to claim 1, wherein the plurality of actuation components includes at least three of: a plurality of articulation cables; one or more electrical lead wires; a drive bar; or a drive tube.

4. The robotic surgical instrument according to claim 1, wherein the plurality of actuation components includes each of: a plurality of articulation cables; one or more electrical lead wires; a drive member; and a drive tube.

5. The robotic surgical instrument according to claim 1, wherein actuating the end effector assembly includes at least one of: articulating the end effector assembly; manipulating the end effector assembly; advancing a component through the end effector assembly; or energizing the end effector assembly.

6. The robotic surgical instrument according to claim 1, wherein the plug is configured to engage the proximal body portion of the proximal link.

7. The robotic surgical instrument according to claim 6, wherein the seal ring is configured to establish at least one of the seals.

8. The robotic surgical instrument according to claim 6, wherein the seal ring includes a plurality of apertures each configured to sealingly receive one of the actuation components of the plurality of actuation components.

9. The robotic surgical instrument according to claim 6, wherein an outer annular surface of the seal ring is configured to seal against the inner annular surface of the shaft.

10. The robotic surgical instrument according to claim 1, wherein the seal configuration extends into an interior of the proximal body portion of the proximal link of the articulating portion of the shaft.

11. A robotic surgical instrument, comprising:
a housing;
a shaft extending distally from the housing and including a proximal segment and an articulating portion extending distally from the proximal segment, the articulating portion including a proximal link and a distal link pivotably coupled to the proximal link, the proximal link including a body portion extending into the proximal segment to define an annular space between an outer annular surface of the body portion of the proximal link and an interior annular surface of the proximal segment of the shaft;
an end effector assembly operably coupled to the articulating portion such that the end effector assembly is configured to articulate relative to the proximal segment of the shaft about the articulating portion;
a plurality of actuation components extending through at least a portion of the shaft to operably couple to the end effector assembly to enable selective actuation of the end effector assembly; and
a seal configuration disposed within the proximal segment of the shaft and extending into an interior of the body portion of the proximal link of the articulating portion, the seal configuration establishing seals within the annular space, about each actuation component of the plurality of actuation components, and within the interior of the body portion of the proximal link of the articulating portion to inhibit fluid communication proximally into the proximal segment of the shaft, wherein the seal configuration includes an engagement plug, an inner seal plug, and an outer seal ring arranged concentrically relative to one another and the proximal segment of the shaft, wherein the engagement plug includes a base disposed within the proximal segment of the shaft proximally of the body portion of the proximal link and first and second arms extending distally from the base into an annular space defined between the body portion of the proximal link and the proximal segment of the shaft to engage the body portion of the proximal link.

12. The robotic surgical instrument according to claim 11, wherein the plurality of actuation components includes at least two of: a plurality of articulation cables; one or more electrical lead wires; a drive bar; or a drive tube.

13. The robotic surgical instrument according to claim 11, wherein the plurality of actuation components includes at least three of: a plurality of articulation cables; one or more electrical lead wires; a drive bar; or a drive tube.

14. The robotic surgical instrument according to claim 11, wherein the plurality of actuation components includes each of: a plurality of articulation cables; one or more electrical lead wires; a drive member; and a drive tube.

15. The robotic surgical instrument according to claim 11, wherein actuating the end effector assembly includes at least one of: articulating the end effector assembly; manipulating the end effector assembly; advancing a component through the end effector assembly; or energizing the end effector assembly.

16. The robotic surgical instrument according to claim 11, wherein the inner seal plug is disposed within the body portion of the proximal link.

17. The robotic surgical instrument according to claim 11, wherein the inner seal plug and the outer seal ring are configured to cooperate to establish at least one of the seals.

18. The robotic surgical instrument according to claim 11, wherein the outer seal ring includes a plurality of apertures each configured to sealingly receive one of the actuation components of the plurality of actuation components, and wherein the outer seal ring further includes an outer annular surface configured to seal against at least one of the inner annular surface of the shaft or an inner annular surface of the proximal link.

19. The robotic surgical instrument according to claim 11, wherein the inner seal plug includes a plurality of apertures each configured to sealingly receive one of the actuation components of the plurality of actuation components.

* * * * *